(12) United States Patent
Qu et al.

(10) Patent No.: US 8,334,900 B2
(45) Date of Patent: Dec. 18, 2012

(54) APPARATUS AND METHOD OF OPTICAL IMAGING FOR MEDICAL DIAGNOSIS

(75) Inventors: Jianan Qu, Hong Kong (CN); Tao Wu, Hong Kong (CN)

(73) Assignee: The Hong Kong University of Science and Technology, Hong Kong (CN)

(*) Notice: Subject to any disclaimer, the term of this patent is extended or adjusted under 35 U.S.C. 154(b) by 640 days.

(21) Appl. No.: 12/506,028

(22) Filed: Jul. 20, 2009

(65) Prior Publication Data
US 2010/0149315 A1 Jun. 17, 2010

Related U.S. Application Data

(60) Provisional application No. 61/129,800, filed on Jul. 21, 2008.

(51) Int. Cl.
*A61B 1/04* (2006.01)
(52) U.S. Cl. .......................................... 348/68; 382/128
(58) Field of Classification Search .................... 348/68; 382/128
See application file for complete search history.

(56) References Cited

U.S. PATENT DOCUMENTS

| | | | |
|---|---|---|---|
| 2005/0064602 A1* | 3/2005 | Kaufman et al. | 436/164 |
| 2007/0013916 A1* | 1/2007 | Kim et al. | 356/498 |
| 2007/0236766 A1* | 10/2007 | Dickson et al. | 359/18 |
| 2008/0152192 A1* | 6/2008 | Zhu et al. | 382/103 |
| 2009/0046905 A1* | 2/2009 | Lange et al. | 382/128 |
| 2009/0279784 A1* | 11/2009 | Arcas et al. | 382/190 |

OTHER PUBLICATIONS

Balas et al., "A novel optical imaging method for the early detection, quantitative grading, and mapping of cancerous and precancerous lesions of cervix," *IEEE Trans. Biomed. Eng.*, 48 (1): 96-104 (Jan. 2001).
Pogue et al., "Analysis of acetic acid-induced whitening of high-grade squamous intraepithelial lesions," *J. Biomed. Opt.*, 6 (4): 397-403 (Oct. 2001).
Wu et al., "Optical imaging for medical diagnosis based on active stereo vision and motion tracking," *Opt. Express*, 15 (16), 10421-10426 (Aug. 2, 2007).
Wu et al., "Optical imaging of cervical precancerous lesions based on active stereo vision and motion tracking," *Opt. Express*, 16 (15), 11224-11230 (Jul. 11, 2008).

* cited by examiner

*Primary Examiner* — Firmin Backer
*Assistant Examiner* — Jonathan Bui
(74) *Attorney, Agent, or Firm* — Leydig, Voit & Mayer, Ltd.

(57) ABSTRACT

Described herein is a novel 3-D optical imaging system based on active stereo vision and motion tracking for to tracking the motion of patient and for registering the time-sequenced images of suspicious lesions recorded during endoscopic or colposcopic examinations. The system quantifies the acetic acid induced optical signals associated with early cancer development. The system includes at least one illuminating light source for generating light illuminating a portion of an object, at least one structured light source for projecting a structured light pattern on the portion of the object, at least one camera for imaging the portion of the object and the structured light pattern, and means for generating a quantitative measurement of an acetic acid-induced change of the portion of the object.

25 Claims, 30 Drawing Sheets

APPARATUS AND METHOD OF OPTICAL IMAGING FOR MEDICAL DIAGNOSIS

CROSS-REFERENCE TO RELATED APPLICATIONS

This patent application claims the benefit of U.S. Provisional Patent Application No. 61/129,800, filed Jul. 21, 2008, which is incorporated by reference.

TECHNICAL FIELD

The invention relates to three-dimensional imaging and, in particular, to three-dimensional colposcopy imaging systems.

BACKGROUND OF THE INVENTION

Colposcopy is a standard technique to detect early neoplastic growth in cervical tissue. It is a medical diagnostic procedure to examine an illuminated, magnified view of the cervix and the tissues of the vagina and vulva. Many premalignant lesions and malignant lesions in these areas have discernible characteristics which can be detected through this examination technique. It is done using a colposcope, which provides an enlarged view of the areas under examination, allowing the colposcopist to visually distinguish normal from abnormal appearing tissue and take directed biopsies for further pathological examination. The main goal of colposcopy is to prevent cervical cancer by detecting precancerous lesions early and treating them.

Cervical intraepithelial neoplasia (CIN), also known as cervical dysplasia, is the potentially premalignant transformation and abnormal growth (i.e., dysplasia) of squamous cells on the surface of the cervix. Most cases of CIN remain stable, or are eliminated by the host's immune system without intervention. However a small percentage of cases progress to become cervical cancer, usually cervical squamous cell carcinoma (SCC), if left untreated. The major cause of CIN is chronic infection of the cervix with the sexually transmitted human papillomavirus (HPV), especially the high-risk HPV types 16 or 18. Over 100 types of HPV have been identified. About a dozen of these types appear to cause cervical dysplasia & may lead to the development of cervical cancer.

Principles of the colposcopy involve the use of acetic acid, to induce an acetowhitening effect in tissues and to produce the contrast between normal tissues and precancerous lesions for diagnosis. Specifically, acetic acid causes swelling of the epithelial tissue, columnar and any abnormal squamous epithelial areas in particular, leading to a reversible coagulation or precipitation of the nuclear proteins and cytokeratins. Thus, the effect of acetic acid depends upon the amount of nuclear proteins and cytokeratins present in the epithelium. When acetic acid is applied to normal squamous epithelium, little coagulation occurs in the superficial cell layer, as this is sparsely nucleated. Though the deeper cells contain more nuclear protein, the acetic acid may not penetrate sufficiently and, hence, the resulting precipitation is not sufficient to obliterate the color of the underlying stroma.

Areas of the cervical CIN undergo maximal coagulation due to their higher content of nuclear protein and prevent light from passing through the epithelium. As a result, the subepithelial vessel pattern is obliterated, and less easy to see, and the epithelium appears white. This reaction is termed acetowhitening, and produces a noticeable effect compared with the normal pinkish color of the surrounding normal squamous epithelium of the cervix, an effect that is commonly visible to the naked eye.

Part of the colposcopic process involves grading the CIN. Depending on several factors such as the type of HPV and the location of the infection, the CIN can be classified into one of the three grades. CIN1 (Grade I) indicates the least risky type, representing only mild dysplasia, or abnormal cell growth. This grade corresponds to a low grade squamous intraepithelial lesion result on a Pap test. This corresponds to infection with HPV, and typically will be cleared by immune response in a year or so, though can take several years to clear. CIN2 (Grade II) indicates moderate dysplasia confined to the basal ⅔ of the epithelium. CIN3 (Grade III) indicates severe dysplasia that spans more than ⅔ of the epithelium and may involve the full thickness. This lesion may sometimes also be referred to as cervical carcinoma in situ.

With low-grade CIN, the acetic acid must penetrate into the lower one-third of the epithelium (where most of the abnormal cells with high nuclear density are located). Hence, the appearance of the whiteness is delayed and less intense due to the smaller amount of nuclear protein compared to areas with high-grade CIN or preclinical invasive cancer. Areas of high-grade CIN and invasive cancer turn densely white and opaque immediately after application of acetic acid, due to their higher concentration of abnormal nuclear protein and the presence of large numbers of dysplastic cells in the superficial layers of the epithelium.

Acetowhitening associated with CIN and invasive cancer quickly appears and persists for more than one minute. The acetic acid effect reverses much more slowly in high-grade CIN lesions and in early pre-clinical invasive cancer than in low-grade lesions, immature metaplasia changes. It may last for 2-4 minutes in the case of high-grade lesions and invasive cancer.

As previously stated, the main goal of colposcopy is to detect the presence of high-grade CIN and invasive cancer. To effectively achieve this, the entire epithelium at risk should be well visualized, abnormalities should be identified accurately and assessed for their degree of abnormality, and appropriate biopsies must be taken. The colposcopic documentation and the biopsies taken by a colposcopist are important indicators for quality management in colposcopy clinics.

The diagnostic criteria of colposcopy based on acetowhitening are subjectively related to the following parameters: the rapidity and length of the acetowhitening processes, the degree of acetowhiteness when the change of color reaches maximum, and the sharpness of the demarcation line between the precancerous lesions and normal tissues. The diagnostic accuracy depends on how an individual colposcopist applies these guidelines during the diagnosis. Therefore, an objective diagnostic procedure based on quantitative measurement of the acetowhitening process is desirable.

The dynamic process of acetowhitening can assist in discriminating the normal and abnormal cervical tissue, even for distinguishing the different grades of CIN. However, as the patient does not reliably remain completely stationary and the camera may be moved by the colposcopist during the colposcopy procedure, which normally takes several minutes, the pixel coordinates of the area of interest in time-sequenced images will change. Slight motion of the patient will cause the loss of the correspondence between the time-sequenced images of cervix recorded during the examination. Without image registration prevented by movement of the patient and/or camera, the measurement of acetowhitening kinetics using the time-sequenced images generates false diagnostic information. Therefore, accurate registration of the time-sequenced images during colposcopy procedure is crucial for accurately measuring the kinetics of acetowhitening in the area of interest.

In image registration for compensating the patient motions during medical diagnosis, it is ideal to make use of the natural features, such as the external Os region (i.e., the opening of the ectocervix) and the transformation zone, for the purpose of image tracking and registration. However, it has been found that these features are not reliable and lack contrasts. For example, the Os is located in the center of the cervix. But it is not always open and its boundary is generally not clear. What is more, previous studies show that the boundary between the transformation zone and the ectocervix is generally not clear. A common approach to visualize the boundary is to apply acetic acid to generate the contrast between the transformation zone and the ectocervix. However, the boundary fades away quickly as the decay of the contrast is induced by the applied acetic acid. This makes the features of the transformation zone unreliable for motion tracking.

Furthermore, because most of the lesions develop within or near the transformation zone, after the acetic acid is applied, the whitened tissue areas (i.e., the CIN lesions) introduce severe interferences and errors to identifying the boundaries of the Os and transformation zone. Therefore, even though the boundaries of the Os and the transformation zone can be identified in some cases, these features are not reliable because they overlap with the acetowhitened tissue areas that are constantly changing during the acetowhitening process. Moreover, due to the patient's motion, three-dimensional rotations cannot be compensated for by using the rigid two-dimensional image registration. Non-rigid image registration may correct the errors caused by the three-dimensional rotation. However, it is much more complicated and may induce more errors than the rigid method.

SUMMARY OF THE INVENTION

An object of the invention is to provide an imaging system and method suitable for colposcopic imaging, where the acetowhitening process is quantitatively measured by combining three-dimensional (3-D) imaging information and motion tracking information. The system employs a three-dimensional optical imaging approach based on the active stereo vision for actively controlling a light source to cast light with a certain spatial pattern, thereby measuring the surface structure of imaged objects. Stereo vision systems utilizing apparatus in addition to cameras for depth estimation are called active stereo vision system and they are distinguished from systems only relying on cameras, which are called passive stereo vision system. The difficulty in passive stereo vision systems for 3-D sensing includes the problem of occlusion and that very few feature points are available when imaging an object having a smooth surface, such as the human cervix. To overcome these problems, the active stereo vision system described herein projects feature points on an imaged object using a structured light. In the field of active stereo vision, a structured light refers to a light source for casting a light pattern onto the object that is being illuminated. The light pattern can take an array of forms including stripes, grids, dots, etc.

This system significantly reduces the complexity of the 3-D surface reconstruction problem and particularly improves the shape reconstruction of objects having plain spatial characteristics such as human tissue. The imaging method and system can be used for reconstructing the surface of objects such as the cervix with relatively plain spatial characteristics. However, one skilled in the art will understand, after reading the description, that the system and method described herein can readily be used for a wide array of applications in addition to colposcopy, including lesion examinations of skin, oral cavities, and internal organs such as the esophagus.

In general, the imaging system projects a structured light pattern onto the imaged object for generating feature points, measures the feature points, and uses them for reconstructing the surface topology of the imaged object.

Specifically, the system includes a projection channel for producing and projecting the structured light having a specific pattern such as a grid pattern onto the imaged object. This light pattern indicates the features points on the surface of the object that will be measured through the imaging channel. The imaging channel collects signals from the imaged object that include 3-D topological information of the object surface represented by the feature points. These collected signals are then used to reconstruct the three-dimensional surfaces of the object.

Furthermore, in order to compensate for movement of the object being imaged, the three-dimensional surfaces are measured at different times. Motion information is derived from this image sequences and, then used for registering the time-sequenced images. In the case of imaging the cervix, the time-sequence images are recorded right after the application of the acetic acid and continuously throughout the acetowhitening process. The ratio of the registered image to the image recorded right after the application of acetic acid provides a map of acetic acid induced changes over the imaged cervix surface.

According to some embodiments, a system is provided for optical imaging in a medical diagnosis. The system includes at least one illuminating light source for generating light illuminating a portion of an object; at least one structured light source for projecting a structured light pattern on the portion of the object; at least one camera for imaging the portion of the object and the structured light pattern; and means for generating a quantitative measurement of an acetic acid-induced change of the portion of the object. Additionally, the system may further include means for performing a diagnosis utilizing the quantitative measurement.

In one embodiment, the at least one camera generates first and second images of the portion of the object and the system further includes means for registering the second image to the first image.

In some embodiments, the acetic acid-induced change includes an acetowhitening process. The quantitative measurement is indicative at least one of a rapidity of the acetowhitening process, a duration of the acetowhitening process, an amplitude of an acetowhitening signals associated with the acetowhitening process, a degree of the acetowhiteness process, a contrast of the acetowhitening process, a sharpness of a demarcation line between precancerous lesions and normal tissues, and a degree of an acetowhitening process when a change of a color of the portion of object reaches a maximum.

In some embodiments, the system further includes means for detecting the structured light pattern from images generated by the at least one camera. The at least one camera generates one or more images of the portion of the object and the system further includes a frame grabber for capturing and storing the one or more images. The system further includes means for detecting a three-dimensional motion of the object from images produced by the at least one camera. Additionally, the system further includes means for analyzing a motion of the object based on images generated by the camera, wherein the motion of the object has at least one of six degrees of freedom and the six degrees of freedom include three degrees of translations and three degrees of rotations.

In some embodiments, the at least one structured light source includes a laser light source for generating a laser beam, a holographic grating for diffracting the laser beam, and one or more reflective surfaces for directing the diffracted laser beam. Additionally, the structured light sources are synchronized with the camera. The structured light pattern includes one of a group of dots, a group of lines, a dot matrix, a plurality of stripes, and a grid pattern.

According to some alternative embodiments, a method is provided for optical imaging in a medical diagnosis process. The method includes illuminating a portion of an object, projecting a structured light pattern onto the portion of the object, generating a sequence of images of the illuminating portion of the object, and measuring an acetic acid-induced change of the portion of the object based on the sequence of images. The method further includes detecting a pathological change of the portion of the object based on the measurement.

The method may further include extracting a three-dimensional surface topology of the portion of the subject from the sequence of images, and tracking a three-dimensional motion of the subject. The sequence of images may be cross-polarized reflection images of the portion of the object. Furthermore, the sequence of images may include a first image and a second image, and the method further includes registering the second image to the first image.

According to still some alternative embodiments, one or more computer readable media are provided. The computer readable media include computer codes for instructing one or more digital processor for optical imaging in a medical diagnosis. The computer codes includes instructions for generating illuminating light for illuminating a portion of an object, instructions for projecting a structured light pattern onto the portion of the object, instructions for generating a sequence of images of the illuminated portion of the object, and instructions for measuring an acetic acid-induced change of the portion of the object based on the sequence of images.

The computer codes further includes instructions for classifying the measurement of the acetic acid-induced change in accordance with a multivariate statistical analysis based on one of a Principle Components Analysis (PCA) and a Support Vector Machine (SVM).

BRIEF DESCRIPTION OF THE DRAWINGS

Certain of the drawings described below and submitted herewith comprise photographs or reproductions of photographs derived from in vivo imaging. In keeping with 37 CFR 1.84(b)(1), these photographs or reproductions of photographs constitute the only practical medium for illustrating aspects of the claimed invention.

DETAILED DESCRIPTION OF THE INVENTION

System Overview

Figure 1:
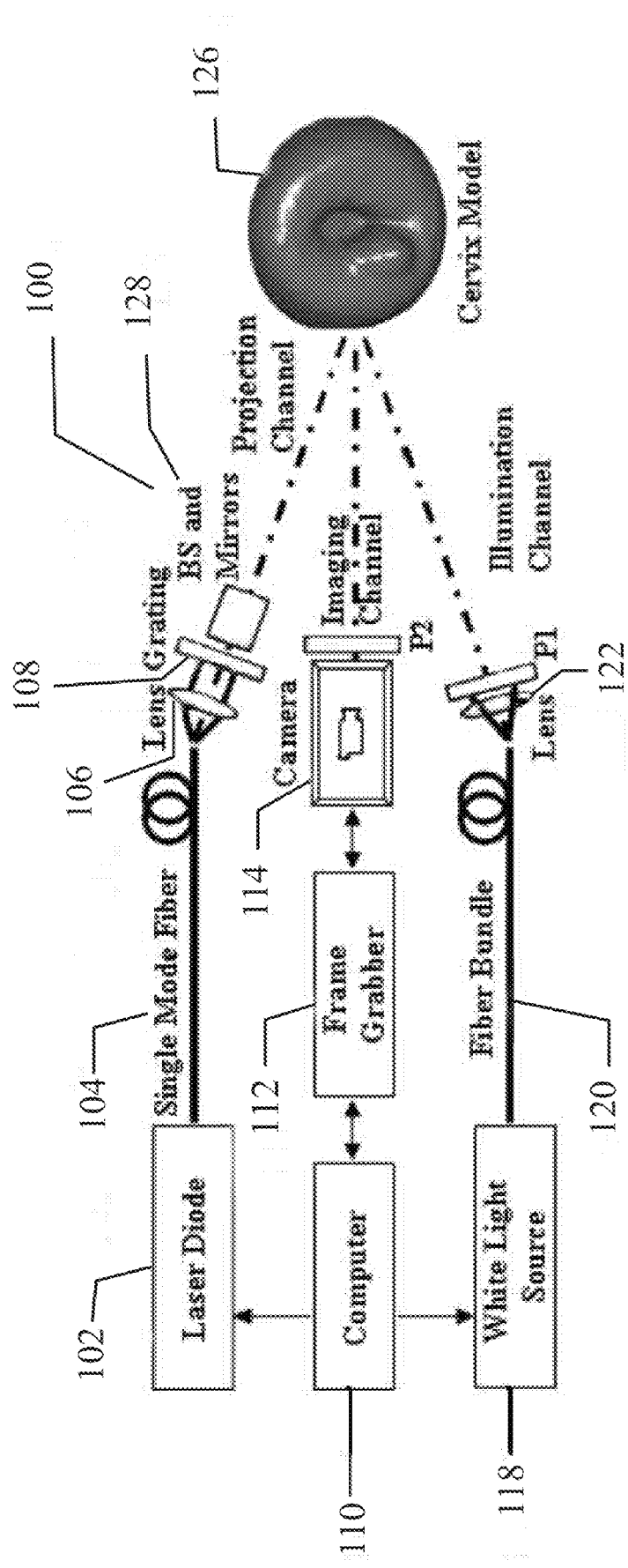
FIG. 1 is a schematic diagram of an apparatus according to one embodiment of the present invention, where P1 and P2 are the polarizers with their polarization orientations perpendicular to each other.

According to one embodiment illustrated in FIG. 1, a system 100 for providing optical imaging for medical diagnosis includes an imaging channel, an illumination channel, and a projection channel. The imaging channel has the similar configuration as a standard colposcope or a low power microscope. A three-CCD color camera 114 and a fast frame grabber 112 are used to capture images with the resolution of 768×576 pixels in the imaging channel. Two polarizers, P1 and P2, with cross-polarization configuration are placed in front of the camera 114 and the white-light illumination source 118, respectively. This arrangement effectively eliminates the specular reflection from the surface of the examined object 126, which is a human cervix model in this exemplary embodiment. The size and shape of the model are similar to a real human cervix. Landmarks indicated by dots on the model surface are used to evaluate the performance of the imaging system in three-dimensional reconstruction of the cervix surface, motion tracking and image registration. The full width and height of the image field-of-view is about 44 mm and 33 mm, respectively.

Figure 2:
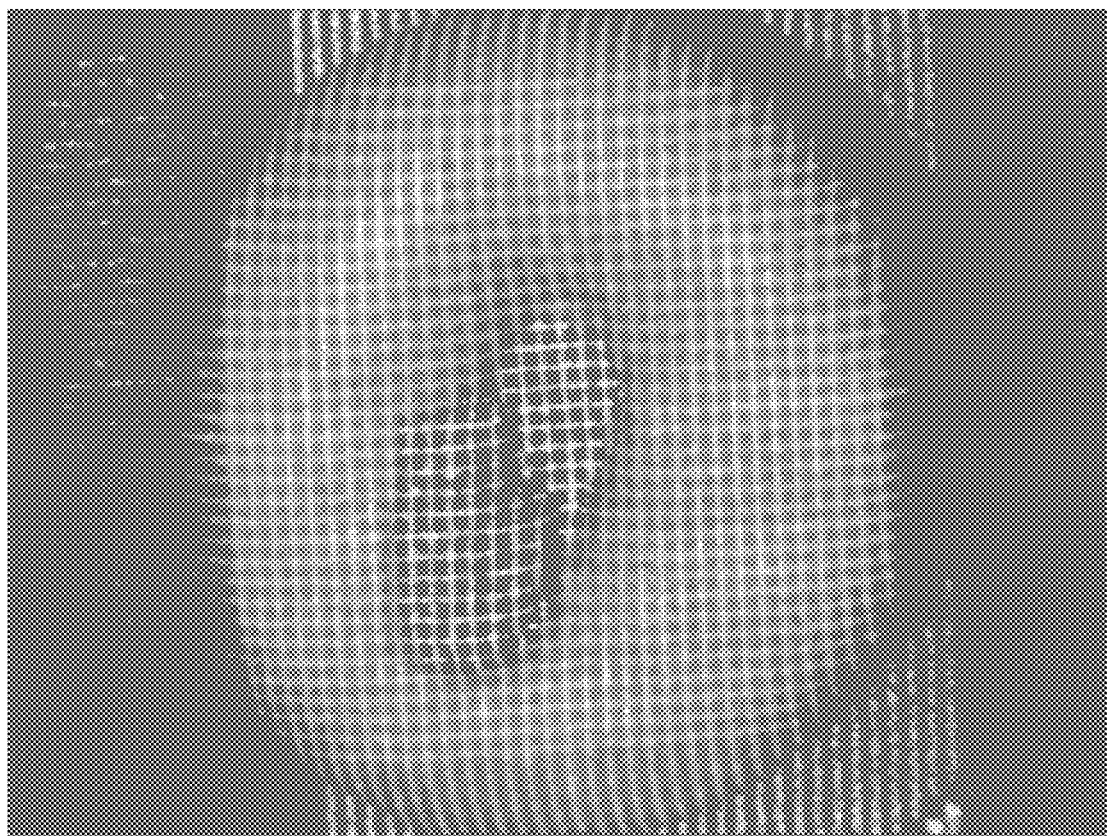
FIG. 2 is a view of a 33×33 grid pattern projected on a cervix model.

In the projection channel, a collimated light source from a 100 mw laser diode 102 at wavelength 660 nm and a holographic grating 108 are used to generate the structured light. The grating converts the collimated beam into 33 stripes with 0.09° separation angle between adjacent stripes. A 50/50 beam splitter (BS) divides the set of stripes into two sets. The orientation of one set of stripes was rotated by 90° using a pair of mirrors. As shown in FIG. 1, the beam splitter and the mirrors are integrated into one unit 128. Alternatively, they can also reside in separate units. A 33×33 grid pattern was formed by the combination of two set of stripes that are perpendicular to each other. The angle between the imaging and projection channel is 8°, about the same as that between the imaging channel and white-light illumination of a standard colposcope. The image of the grid pattern projected on a cervix model is shown in FIG. 2. The spacing of the lines of the grid projected on the cervix model is about 0.82 mm.

System Calibration

The projection and imaging channels of the imaging system 100 were calibrated before the measurement of the three-dimensional surface of the object. The calibration procedures establish the relationship between the coordinates of the imaging system and a real-world coordinate system. Firstly, a Tsai's pinhole camera model as well known in the art was used to calibrate the imaging channel using a non-plane checker board with known three-dimensional feature points. Then, the calibration parameters were used to calculate the three-dimensional coordinates of the grid pattern projected on the same checker board. Finally, the three-dimensional grid will be used for calibrating the projection channel.

The Tsai's calibration model includes a rigid body transformation from a three-dimensional world coordinate system to a two-dimensional image coordinate system. It follows a projection of pinhole camera geometry from a 3-D real-world coordinate system to the ideal image coordinates in the plane of the CCD camera sensor. The ideal image coordinates are then transformed to the actual image coordinates to characterize the distortion of the imaging system. Finally, the actual image coordinates are related to image pixels based the knowledge of the CCD camera 114 and the frame grabber 112. This technique is commonly used in the field of camera calibration, and the details of Tsai's calibration method are presented in R. Y. Tsai, "A versatile camera calibration technique for high accuracy 3D machine vision metrology using off-the-shelf TV camera and lenses," IEEE J. Rob. Autom. 3, 323-344 (1987).

Figure 3:
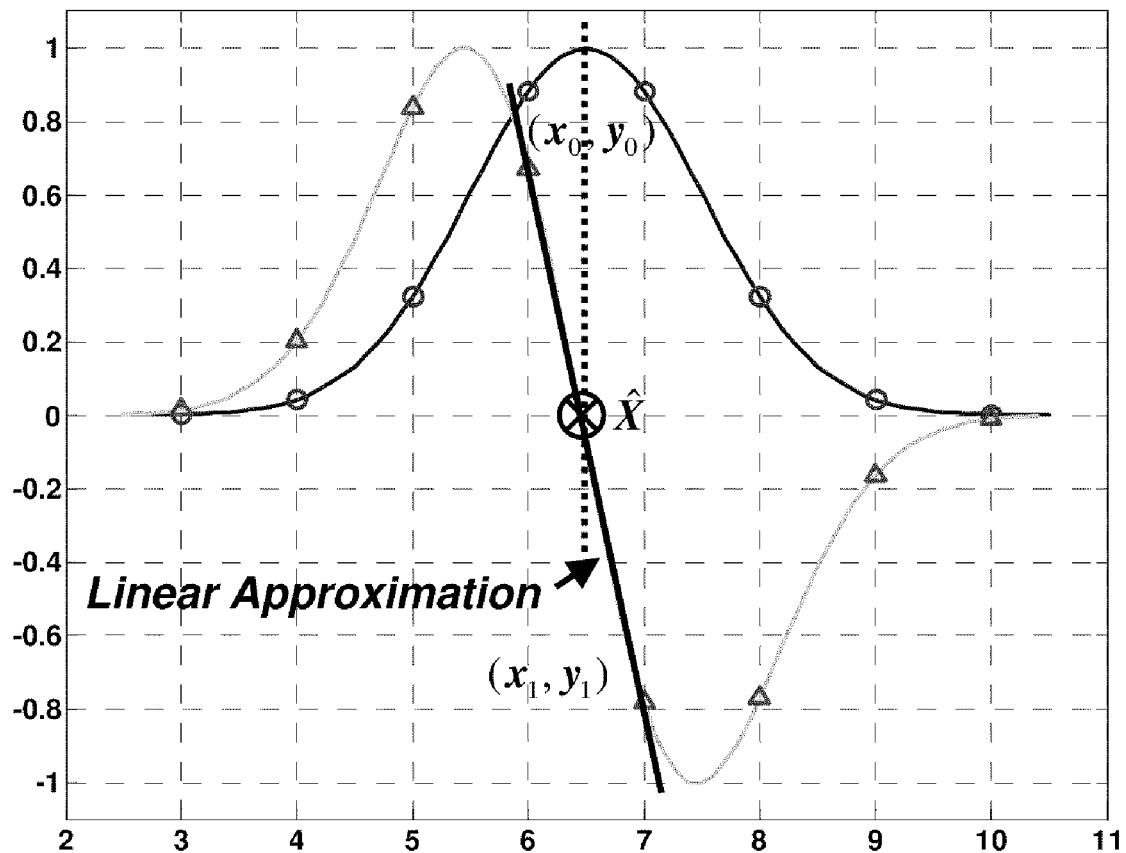
FIG. 3 illustrates the laser peak detection, where the curve with circular marks indicates the Gaussian power profile and the curve with triangular marks indicates the first derivative.

In calibrating the projection channel, the grid pattern is projected on the same checker board used in the calibration of the imaging channel. The checker board includes two orthogonal surfaces with known plane equations. Because each laser stripe can be modeled as a fan plane emitted from the laser center, the grid pattern is considered as the intersections of the fan planes of all laser stripes with the checker board. The three-dimensional coordinates along the intersection lines on the checker board can be calculated from the image of grid pattern using the camera calibration model and the plane equations of checker board. Thus, the plane equations of all stripes can be determined using the three-dimensional coordinates of the intersection lines. The first step in the projection channel calibration procedure is the detection of the centers of each laser stripe. The laser stripe is generated using a diode laser with an optical grating and focal lens which yields an approximate Gaussian power profile along the cross-section to the laser stripes. To accurately detect the position of the centers of the laser stripes, we use a subpixel peak detection detect method as depicted in FIG. 3. By taking the first derivative of the Gaussian power profile of the laser stripe in a noise-free experiment, the point at which the first derivative crosses the zero of the axis is the peak location, as shown in FIG. 3.

Figure 4A:
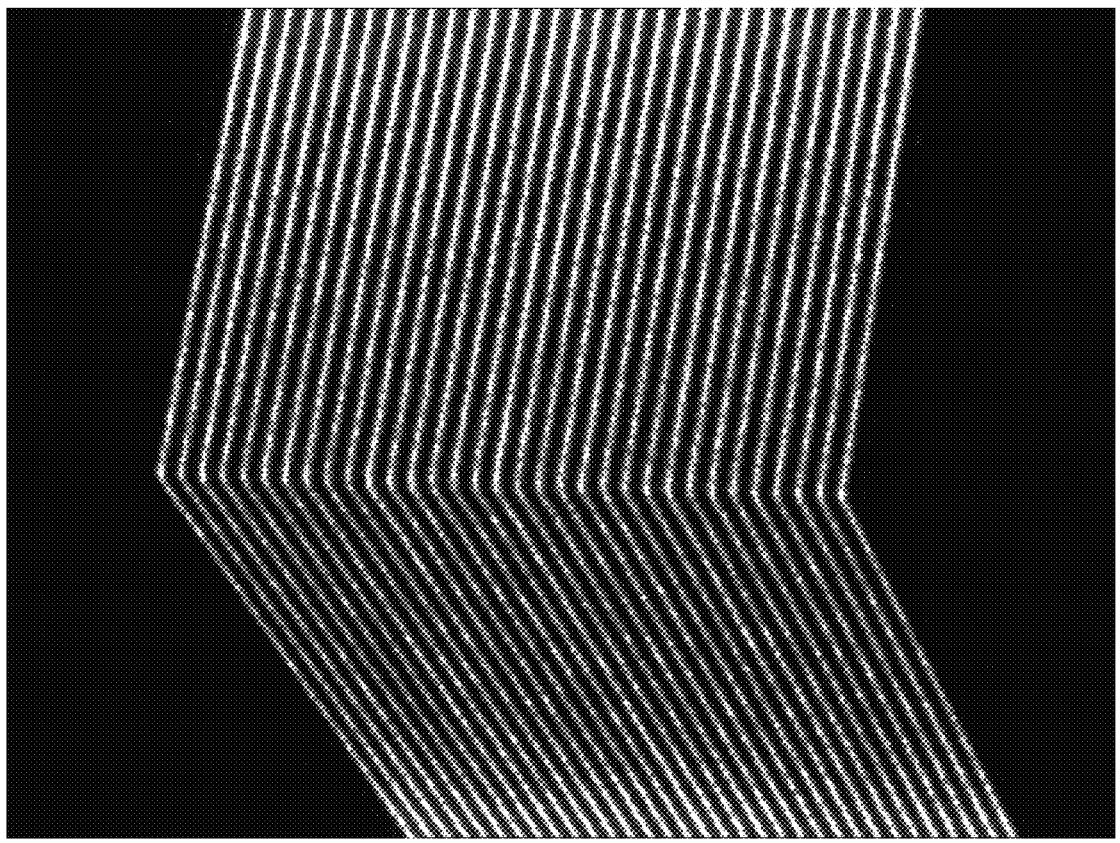
FIG. 4(a) is a graph that illustrates one set of the laser stripes projected onto a surface having two perpendicular faces.
Figure 4B:
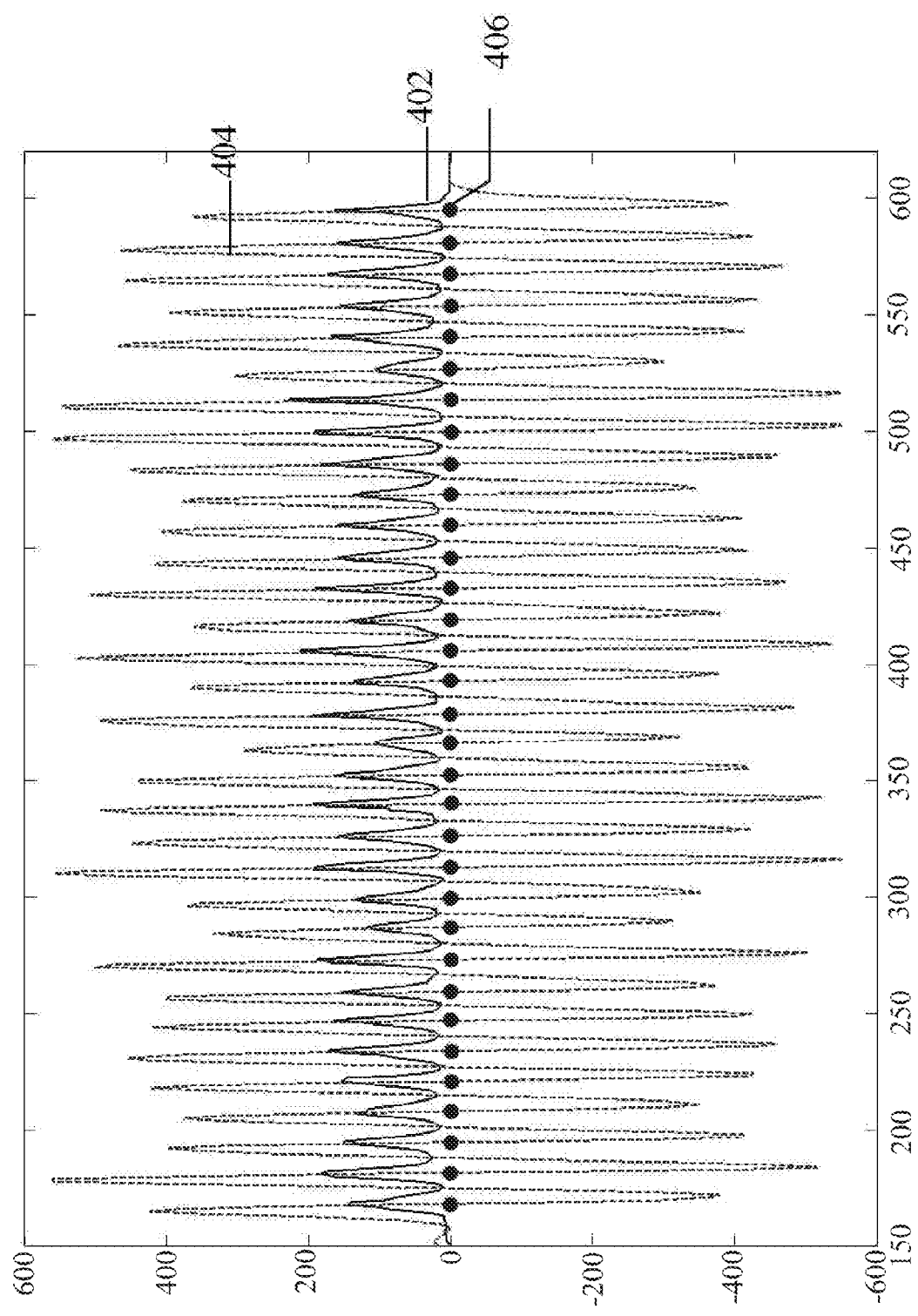
FIG. 4(b) is a graph that depicts the detected centers at one row in the image shown in FIG. 4(a) where the solid curve 402 indicates the laser stripe intensity along the row, the dashed curve 404 indicates the first derivative, and circles 406 indicates the detected peak positions.
Figure 4C:
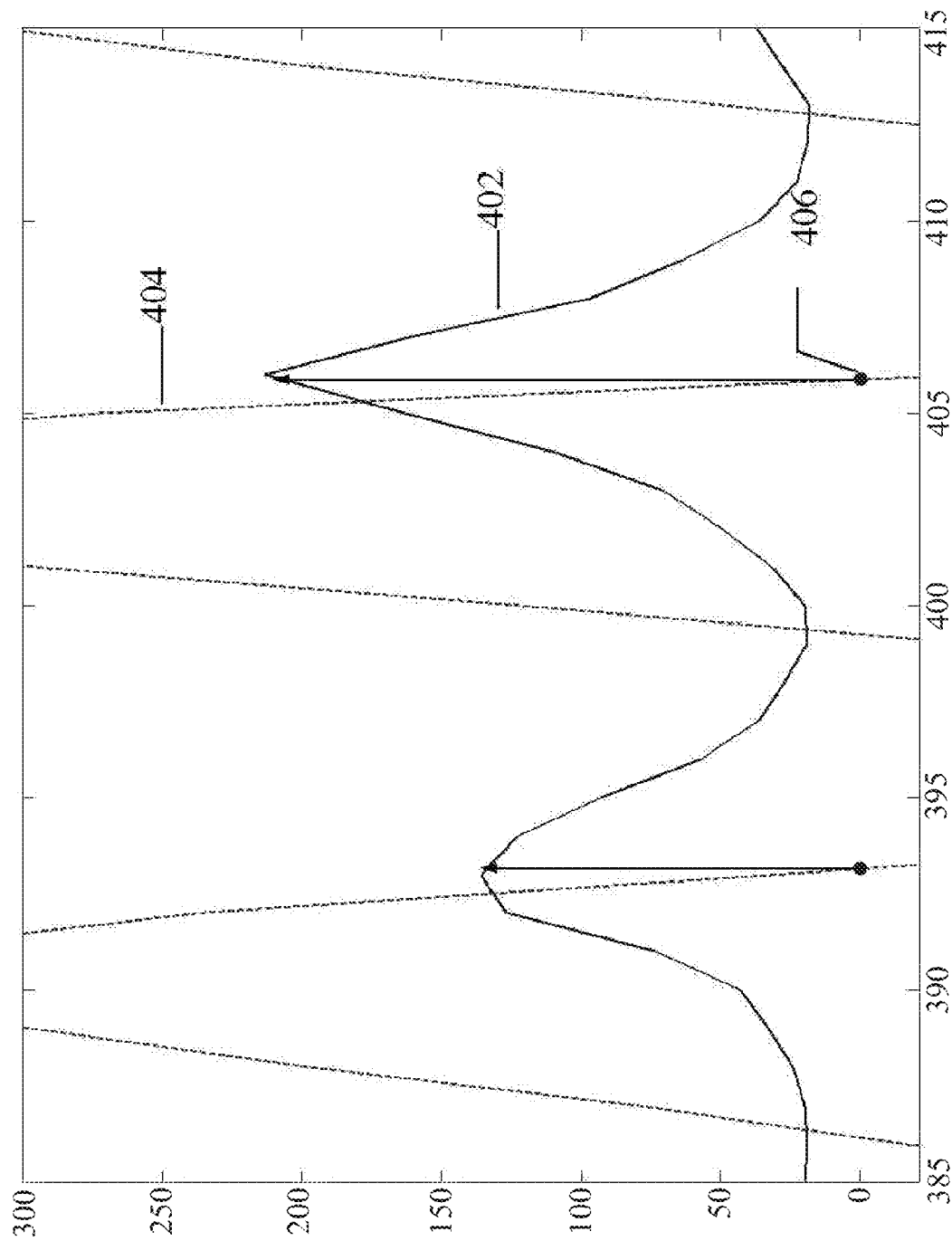
FIG. 4(c) is a graph that depicts an enlarged view of two peaks of the laser stripe intensity of FIG. 4(b)

In our study, a pre-processing is used to remove the additional lines generated by the grating and to remove additive noises from the picture as shown in FIG. 4(a). The best center detection is always obtained with the Forest method with a 4th to 6th order filter as shown in FIG. 4(b). An enlarged view of a portion of FIG. 4(b) is shown in FIG. 4(c), demonstrating the accuracy of the peak detection. When the laser stripes are too close to each other, some false peaks may be detected by the zero-crossing of the first derivative. Therefore, the second derivative is used, indicating the maximum value to eliminate the false peaks. After the center points are determined on each of the laser stripe, their three-dimensional coordinates are determined relative to the camera coordinate system by triangulation. Finally, the plane coefficients can be determined by fitting a three-dimensional plane to the three-dimensional points using a least-squared method. The three-dimensional plane fitting error is 0.013±0.010 mm for all the 66 planes. So far, both the imaging and projection channels are well-calibrated. Their relative displacement and orientation are known and hence are ready for the three-dimensional reconstruction.

Figure 5:
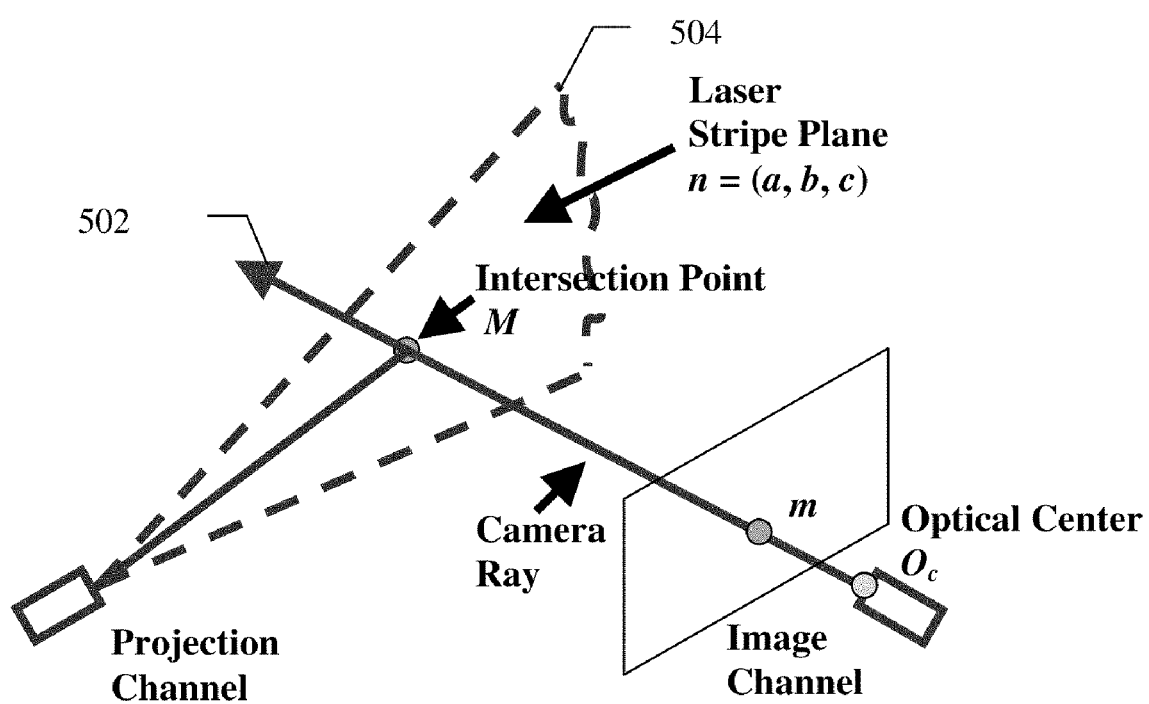
FIG. 5 is an illustration of the triangulation between a fan plane forming the laser stripe and a three-dimensional line connecting the optical center of the camera and an image point.

Three-Dimensional Surface Reconstruction, Image Registration, and Motion Tracking To perform the three-dimensional surface measurement, the correspondence of feature points on the imaged object must be established between the imaging and the projection channels. The three-dimensional topology of the imaged object surface was calculated based on the triangulation of a ray from the imaging channel and a plane from the projection channel. When the 33×33 grid pattern is projected on the object, the spatial arrangement of the stripes is known. The correspondence of the stripes between the imaging and projection channels can be obtained by simply sorting out the stripes in the image according to their spatial arrangement. For the laser stripes projected on the object surface, the points along each stripe are used as the feature points. After the calculation of the plane equation of each stripe and the ray equation of each feature point, the reconstruction problem can be solved based on the triangulation of the ray and plane as shown in FIG. 5. In particular, the intersection point M used for reconstructing the object surface can be calculated based on the linear equation representing the ray 502 and plane 504 as is well known in the art.

Figure 6A:
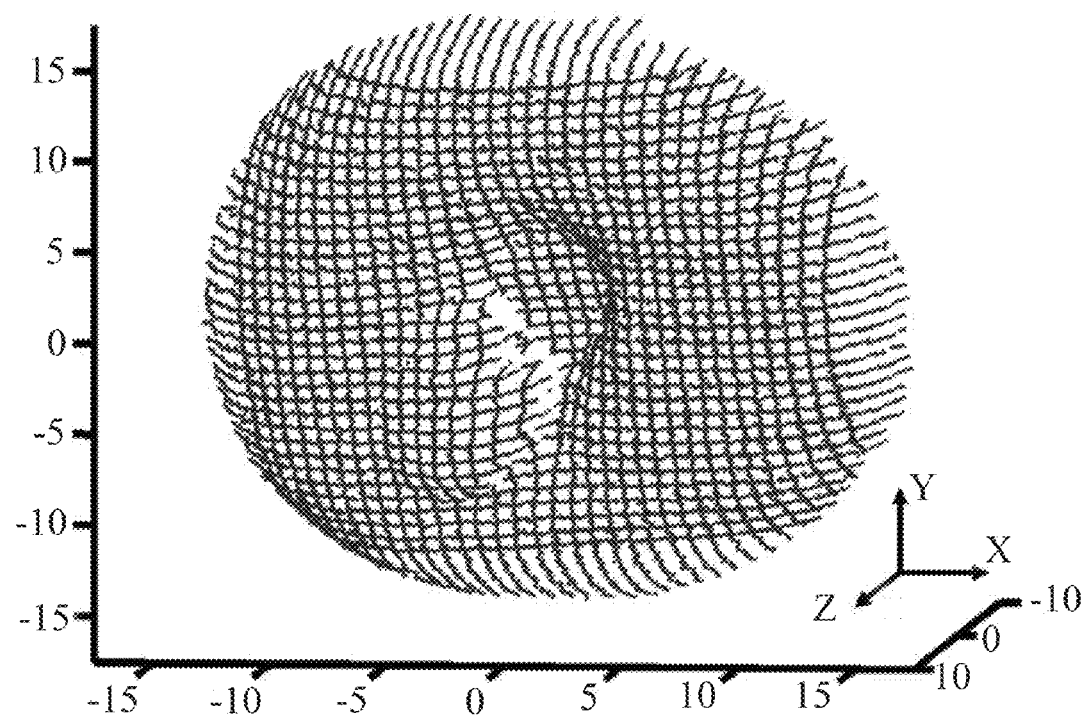
FIG. 6(a) depicts a reconstructed three-dimensional grid projected on the surface of the cervix model, where the unit of scale is millimeter.
Figure 6B:
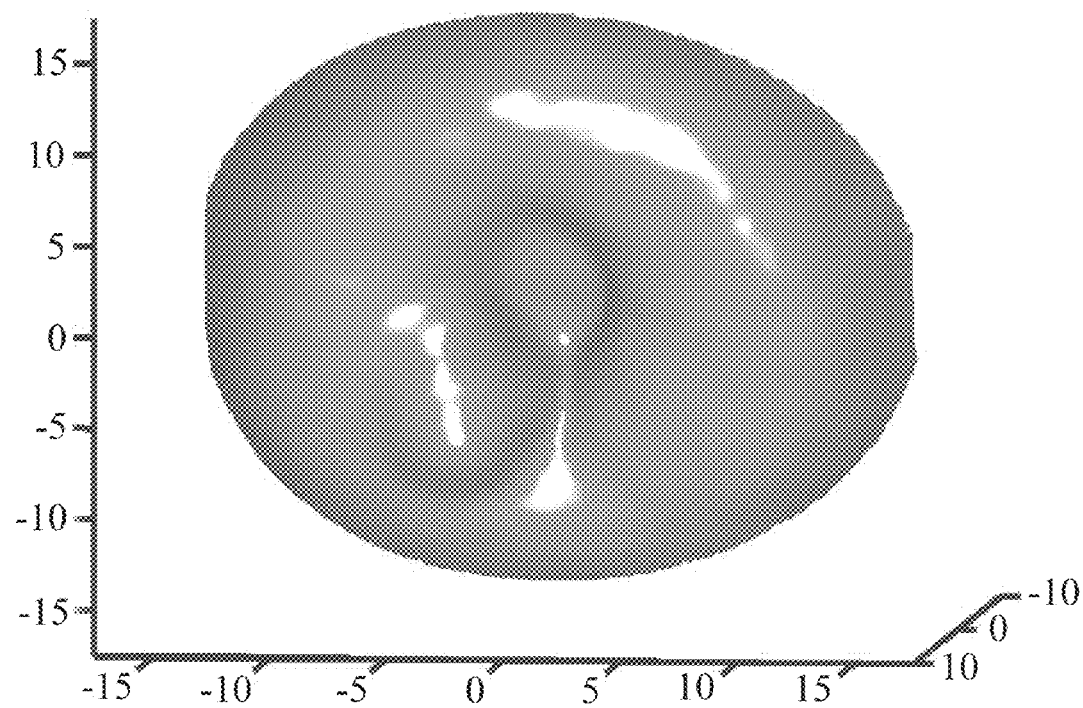
FIG. 6(b) depicts a reconstructed continuous surface using interpolation.

Specifically, the surface of an object can be reconstructed by actively projecting a laser grid on the object's surface, capturing the image through the imaging channel, and then reconstructing the surface by triangulation. The reconstructed grid projected on a cervix model is shown in FIG. 6(a). The corresponding continuous 3-D surface generated by interpolation is shown in FIG. 6(b).

According to a further embodiment, after the three-dimensional information of the cervix model surface is known, the motion of surface at different locations is tracked by using the three-dimensional information. A number of tracking methods can be used for this task where the surfaces of the three-dimensional surface of the cervix model are first registered. Specifically, a continuous reference surface of the cervix model at initial position is constructed. The regions in the reference surface not sampled by the grid pattern are filled up with triangle meshes using interpolations. Targeted surfaces are registered to the reference surface and the three-dimensional surface transformations can be calculated.

Figure 7:
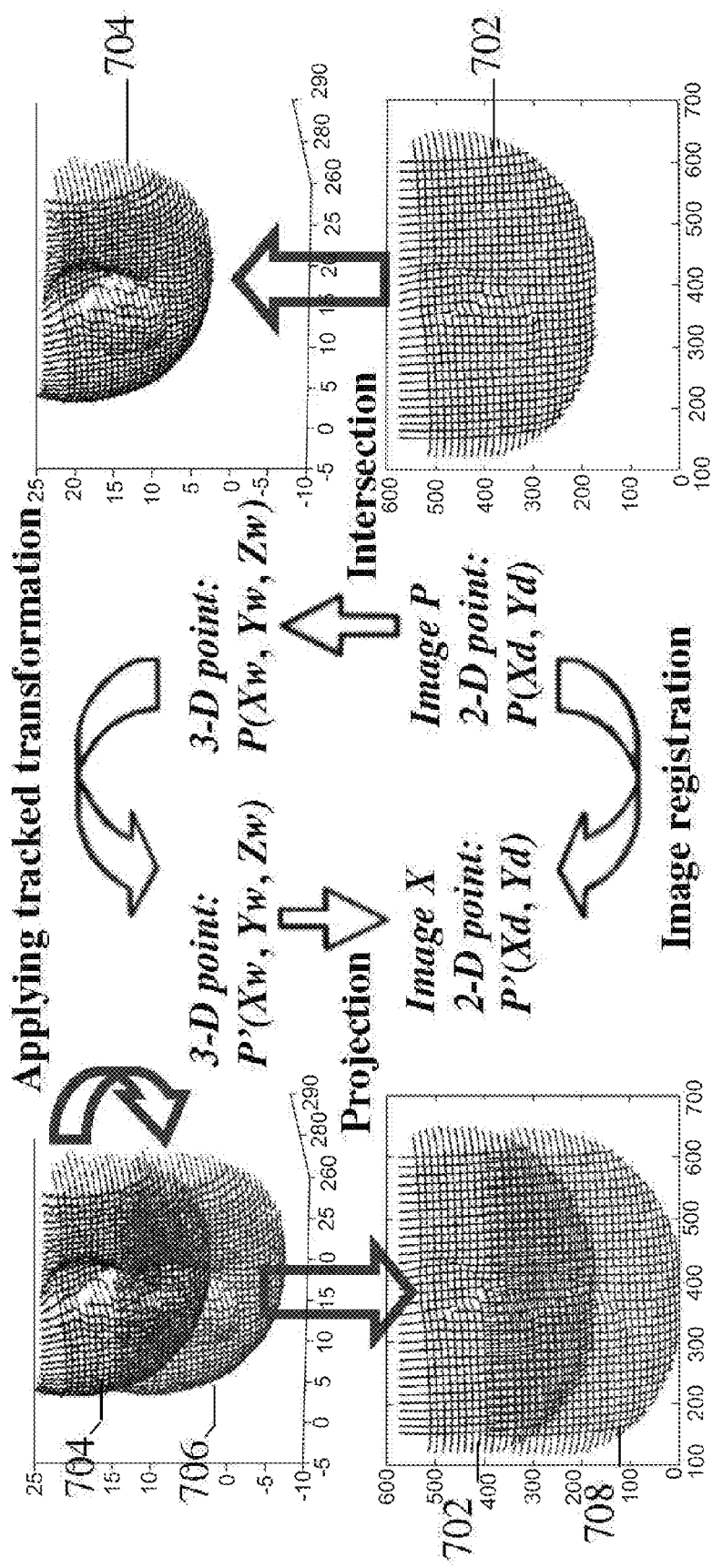
FIG. 7 illustrates a two-dimensional image registration using the three-dimensional transformation (i.e., rotations and translations) provided by the tracking information collected from the object.

After the completion of three-dimensional motion tracking, the registration of 2-D images can be achieved by using the three-dimensional transformation provided by the tracking. FIG. 7 shows a method for registering two-dimensional images by using the three-dimensional transformations provided by the tracking. Firstly, the coordinates of a laser grid point in the image of the target surface, P(Xd, Yd) 702, and in the three-dimensional real-world coordinates, P(Xw, Yw, Zw) 704, are determined. A three-dimensional transformation is applied to P(Xw, Yw, Zw) 704 to obtain the three-dimensional coordinates, P'(Xw, Yw, Zw) 706, which are supposed to be the closest corresponding points in the reference surface. Secondly, the point, P'(Xw, Yw, Zw) 706, is projected onto the two-dimensional image plane to obtain the coordinates, P'(Xd, Yd) 708, in the image of the reference surface using the calibrated camera model. Thirdly, the corresponding points, P(Xd, Yd) 702 and P'(Xd, Yd) 708, are used to calculate the two-dimensional transformation and to register the target image to the reference image. Alternatively, other digital image processing methods can also be used to register the two-dimensional images without relying on the three-dimensional tracking information.

Specifically, feature points of the reference and targeted two-dimensional images are extracted by using an edge or corner detection algorithm. Then the image registration can then be performed based on the similarity between the two sets of feature points. The common edge and corner detection algorithms that can be utilized for extracting the feature points includes Canny edge detection, differential edge detection, thresholding, Sobel edge detection, etc.

An Alternative Embodiment of the Imaging System

Figure 8:
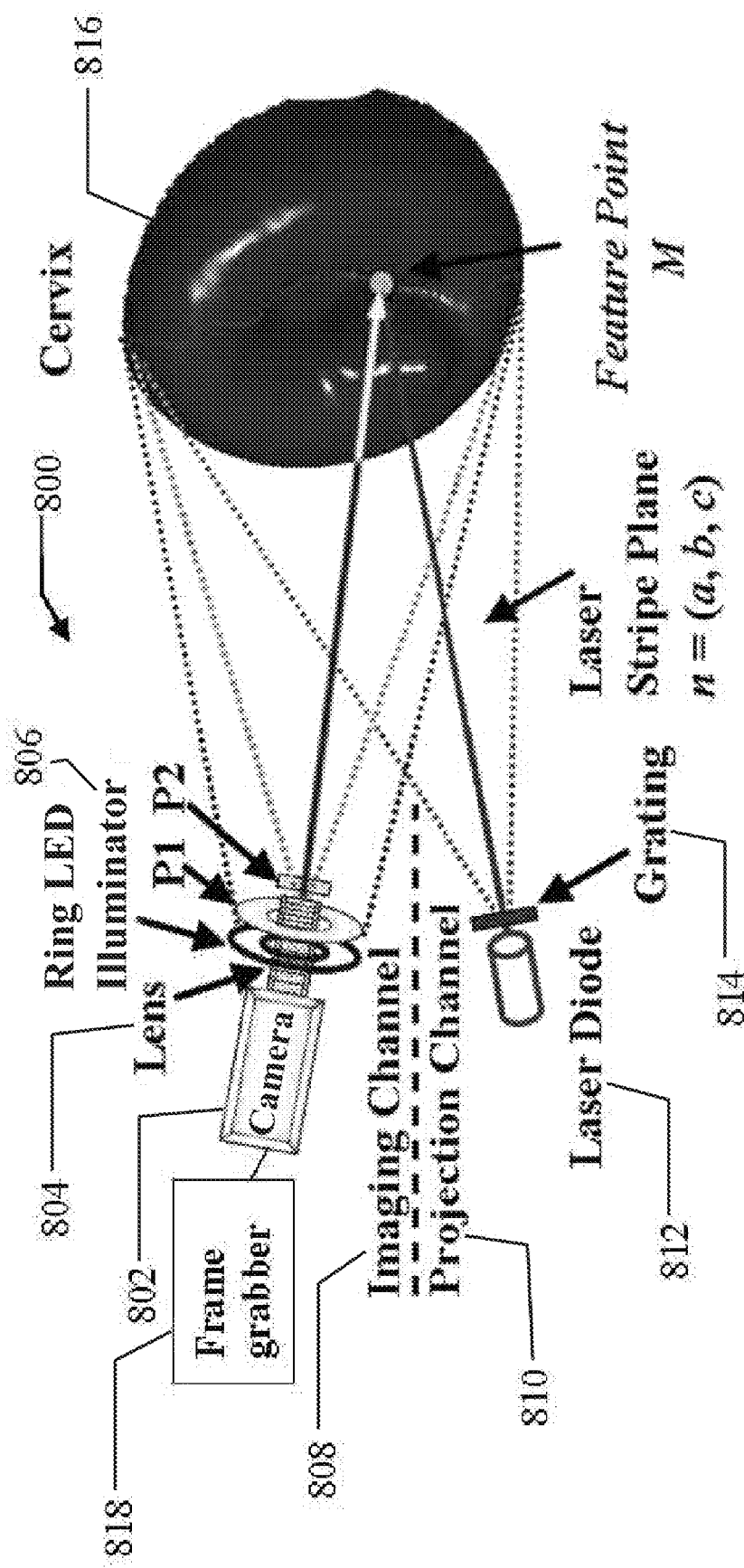
FIG. 8 shows a schematic view of an apparatus according to another embodiment of the present invention, where P1 and P2 are the polarizers with their polarization orientations perpendicular to each other.

According to another embodiment, the illumination optics and the collection optics are integrated co-axially to prevent casting shadow on the examined tissue, as depicted in FIG. 8. Specifically, the imaging channel 808 was designed with a similar configuration as that of a standard digital colposcope. A three-CCD color camera 802 and a fast frame grabber 816 were used to capture images with the resolution of 768×576 pixels in the imaging channel 808. The illumination channel (not shown) includes a ring illuminator 806 and a linear polarizer P1. The ring illuminator 806 with 30 blue-light LEDs produced uniform illumination on the object surface. The polarization direction of the linear polarizer P1 was set to be perpendicular to the polarizer P2 in front of the camera. The cross-polarization arrangement eliminated the specular reflection from the surface of the examined object. In the projection channel 810, a structured light with 33 laser stripes was generated by a laser diode 812 at 660 nm and a holographic grating 814. To make sure that most of the 33 laser stripes can be projected through the speculum used in the colposcopy. The angle between the imaging channel 808 and projection channel 810 was set to about 5°.

Figure 9A:
FIGS. 9 (a) through 9 (d) show (a) a cross-polarized reflection image of a human cervix taken in the blue channel; (b) an image of the laser stripes projected on the human cervix surface; (c) the image of the human cervix surface using a commercial colposcope; and (d) an image of a reconstructed three-dimensional human cervix surface with intensity texture mapping (unit: mm)
Figure 9B:
Figure 9D:
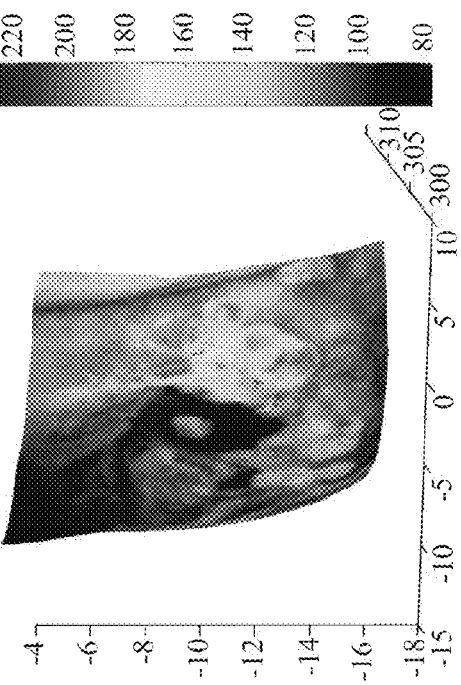
Figure 9C:

Because the patient's motion is continuous, the images of cervix and the projected laser stripe pattern on cervix must be taken simultaneously. The blue and red channels of the three-CCD color camera 802 are used to capture the images of the cross-polarized reflection and the laser stripe pattern, respectively. Typical image of a cervix surface illuminated by the blue-light ring illuminator and the image of laser stripes on cervix are shown in FIGS. 9(a) and (b). The field-of-view of the image is about 37 mm by 28 mm. The resolution of the imaging system is about 0.05 mm/pixel. The image from the same subject imaged by a commercial colposcope is shown in FIG. 9(c) as a reference.

The projection and imaging channels of the imaging system were calibrated before the measurement of the three-dimensional surface of the cervix. The three-dimensional topology of the imaged cervical surface was calculated based on the triangulation between a ray from the imaging channel 808 and a plane from the projection channel 810. A reconstructed three-dimensional cervix surface is shown in FIG. 9(d). After the three-dimensional information of the cervix surface was known, the motion of the surface at different locations is tracked. The registration of two-dimensional images taken during the examination was achieved by using the three-dimensional transformation provided by the motion tracking. As discussed earlier, other digital image processing method can also be used to register the two-dimensional images without using the three-dimensional information.

System Evaluation Based on a Cervix Model

As shown in FIG. 1, a human cervix model is used to evaluate the accuracy of the motion tracking and image registration. The human cervix model is mounted on a multi-dimensional translation and rotation stage providing precise motions of translation and rotation along the X, Y, and Z axes of the stage, respectively. The Z axis is parallel to the optical axis of the imaging channel and the origin of the stage coordinates is about 280 mm from the imaging system, which is a typical working distance of a standard colposcope.

A total of 26 landmarks evenly distributed on the surface of the cervix model are used for the performance evaluation. A quaternion method is used to determine the actual motions. It provides a standard for the evaluation of motion tracking results produced by the motion tracking algorithm. The accuracy of quaternion method is mainly determined by the measurement error of the three-dimensional imaging system.

Figure 10:
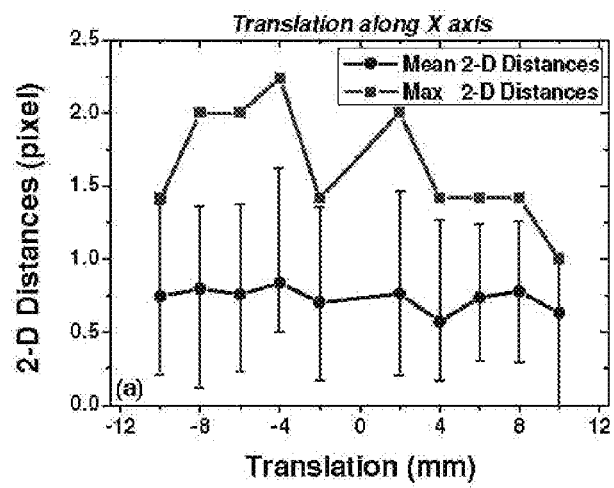
FIGS. 10 (a) through 10 (f) illustrate (a) the mean and max distances vs. the translation along the X axis; (b) the mean and max distances vs. the translation along the Y axis; (c) the mean and max distances vs. the translation along the Z axis; (d) the mean and max distances vs. the rotation along the X axis; (e) the mean and max distances vs. the rotation along the Y axis; (f) the mean and max distances vs. the rotation along the Z axis, where the blue curves with circles indicates mean distances and red curves with squares indicates max distances.
Figure 10:
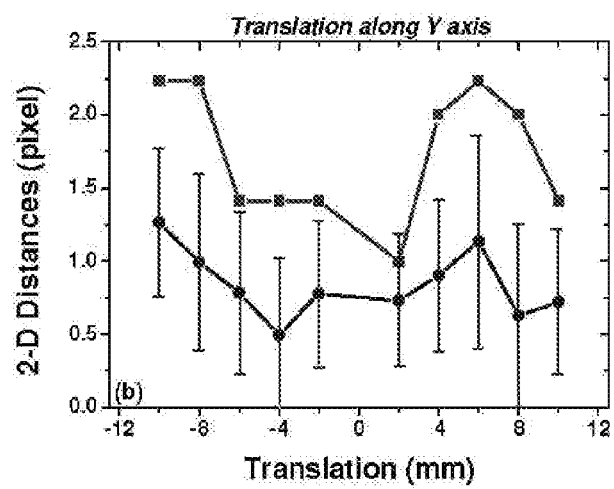
Figure 10:
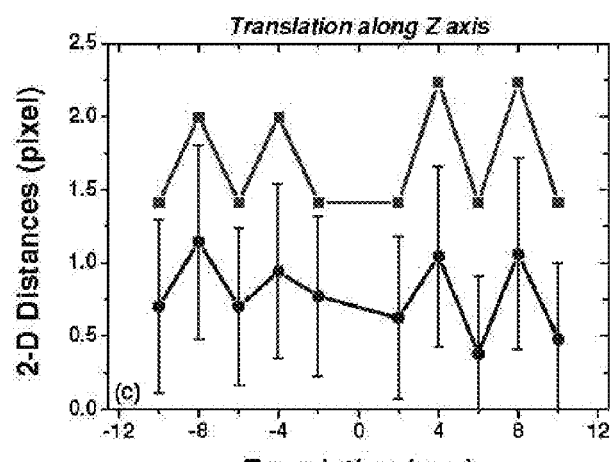
Figure 10:
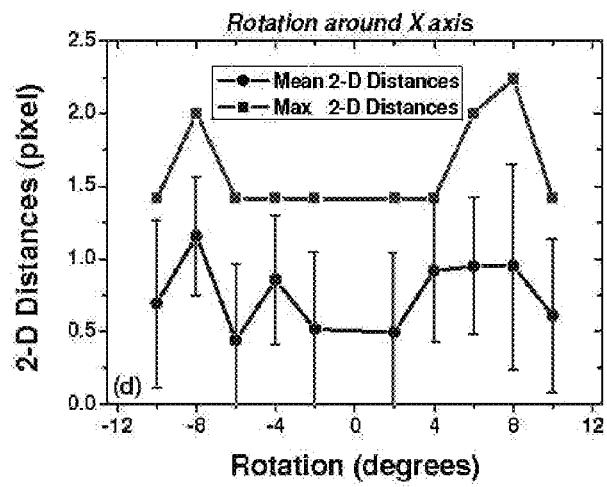
Figure 10:
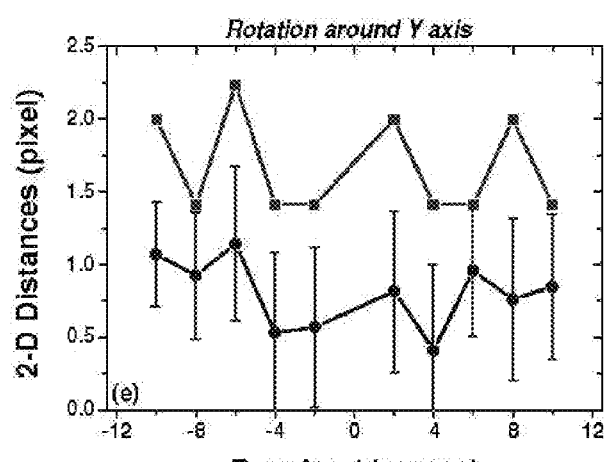
Figure 10:
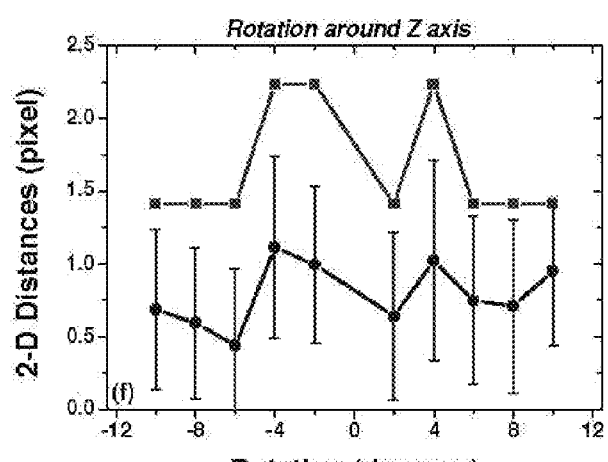

We evaluated the performance of the three-dimensional imaging system, motion tracking algorithm and image registration method by creating a series of translations along and rotations around the X, Y, and Z axes of the stage coordinates. The motion ranges of the translation and rotation were ±10 mm and ±10 degrees, respectively. These are considered to be large movements of patient during colposcopy procedure because it has been reported that the maximal average patient motion is 4.5 mm. The three-dimensional distances are calculated in mm and the two-dimensional distances in pixel between the landmarks on the reference surface and the target surface after quaternion and the tracked transformation are applied, respectively. The performance evaluations were based on the comparison between the mean distances over the motion ranges calculated by using the quaternion and motion tracking algorithms, respectively. The results are summarized in Table 1 and the two-dimensional distance versus the transformation curves are shown in FIG. 10.

TABLE 1

Comparison of quaternion and motion tracking results.

| Motions in stage coordinates | Mean 3-D distances (mm) | | Mean 2-D distances (pixel) | |
|---|---|---|---|---|
| | Quaternion | Motion Tracking | Quaternion | Motion Tracking |
| X - Translation | 0.10 ± 0.08 | 0.13 ± 0.09 | 0.49 ± 0.53 | 0.73 ± 0.57 |
| Y - Translation | 0.14 ± 0.10 | 0.16 ± 0.11 | 0.42 ± 0.52 | 0.84 ± 0.57 |
| Z - Translation | 0.13 ± 0.09 | 0.15 ± 0.10 | 0.35 ± 0.50 | 0.78 ± 0.63 |
| X - Rotation | 0.10 ± 0.07 | 0.11 ± 0.07 | 0.53 ± 0.54 | 0.72 ± 0.58 |
| Y - Rotation | 0.11 ± 0.08 | 0.13 ± 0.09 | 0.42 ± 0.46 | 0.81 ± 0.53 |
| Z - Rotation | 0.11 ± 0.10 | 0.14 ± 0.12 | 0.31 ± 0.49 | 0.79 ± 0.60 |

As can be seen, the mean three-dimensional distance over the ranges of translational and rotational motions is less than 0.14 mm for quaternion method and less than 0.16 mm for the motion tracking algorithm, respectively. With the image registration the mean two-dimensional distance is less than 0.53 pixels for quaternion method and 0.84 pixels for the motion tracking algorithm. The accuracy of the motion tracking algorithm is comparable to the accuracy of the quaternion method.

Figure 11B:
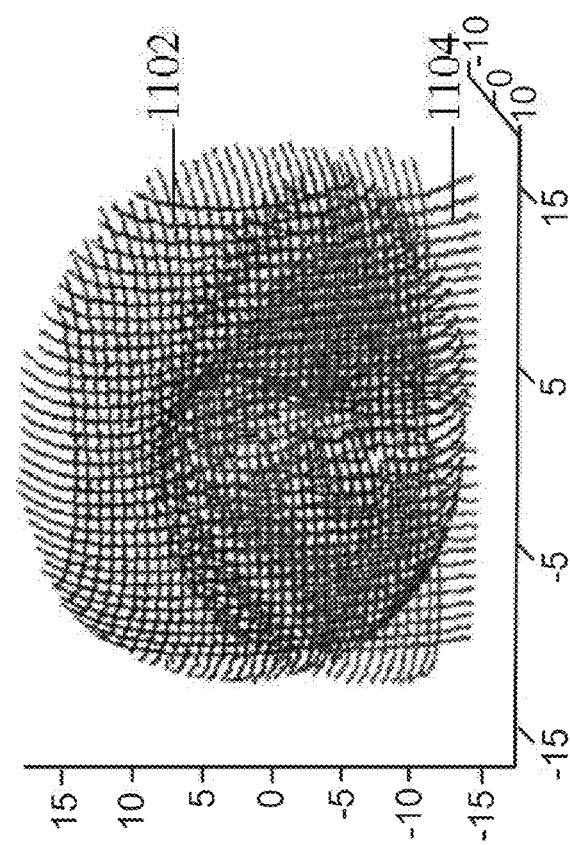
FIGS. 11 (a) and 11 (b) show one representative tracking result with the translation along Y axis: (a) shows superposition of the reference 1102 and registered target 1106 grids of the cervix model; and (b) shows superposition of the reference 1102 and target 1104 grids.
Figure 11A:
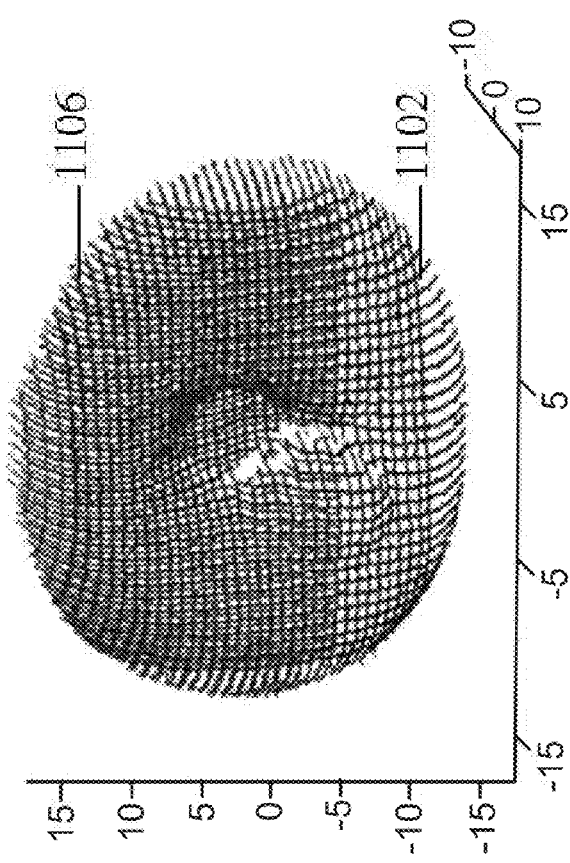

The imaging system and method described herein provide accurate tracking of the motions of a patient and accurate registrations of the time-sequenced images during a colposcopy procedure. A representative result shown in FIG. 11 demonstrates the accurate two-dimensional image registration over the motion range based on the three-dimensional imaging and motion tracking algorithm. The motions include a translation of −10 mm along the Y axis. The three-dimensional grid in FIG. 11(a) is the superposition of the reference 1102 and registered target 1106 grids of the cervix model. The three-dimensional grid in FIG. 11(b) is the superposition of the reference 1102 and target grids 1104. The registered target grid is almost overlapped with the reference grid while the original target grid is far away from the reference one.

The results indicate that the imaging system based on active stereo vision and motion tracking is capable of producing accurate two-dimensional image registration for large motions of the human cervix. The accuracy of the image registration is less than 1 pixel, equivalent to 0.06 mm in the X-Y plane, and is adequate for the measurement of the acetowhitening process from a CIN lesion normally having a size of a few mm.

System Evaluation Based on an In Vivo Study

Fifty-seven human subjects originally scheduled for the examination with colposcopy and loop electrosurgical excision procedure (LEEP) were enrolled in an in vivo study for verifying and evaluating the method and system described herein. The images of the cervix and the structured light were recorded over 5 minutes after the application of the acetic acid. The images in the blue and red channels were stored for the analysis of the acetowhitening kinetics. A routine colposcopy was followed up after the three-dimensional imaging. The colposcopic diagnosis of the examined tissue sites was provided by two colposcopists, and the histological analysis of the tissue biopsy taken from the subjects' cervices was performed by experienced pathologists.

Figure 12:
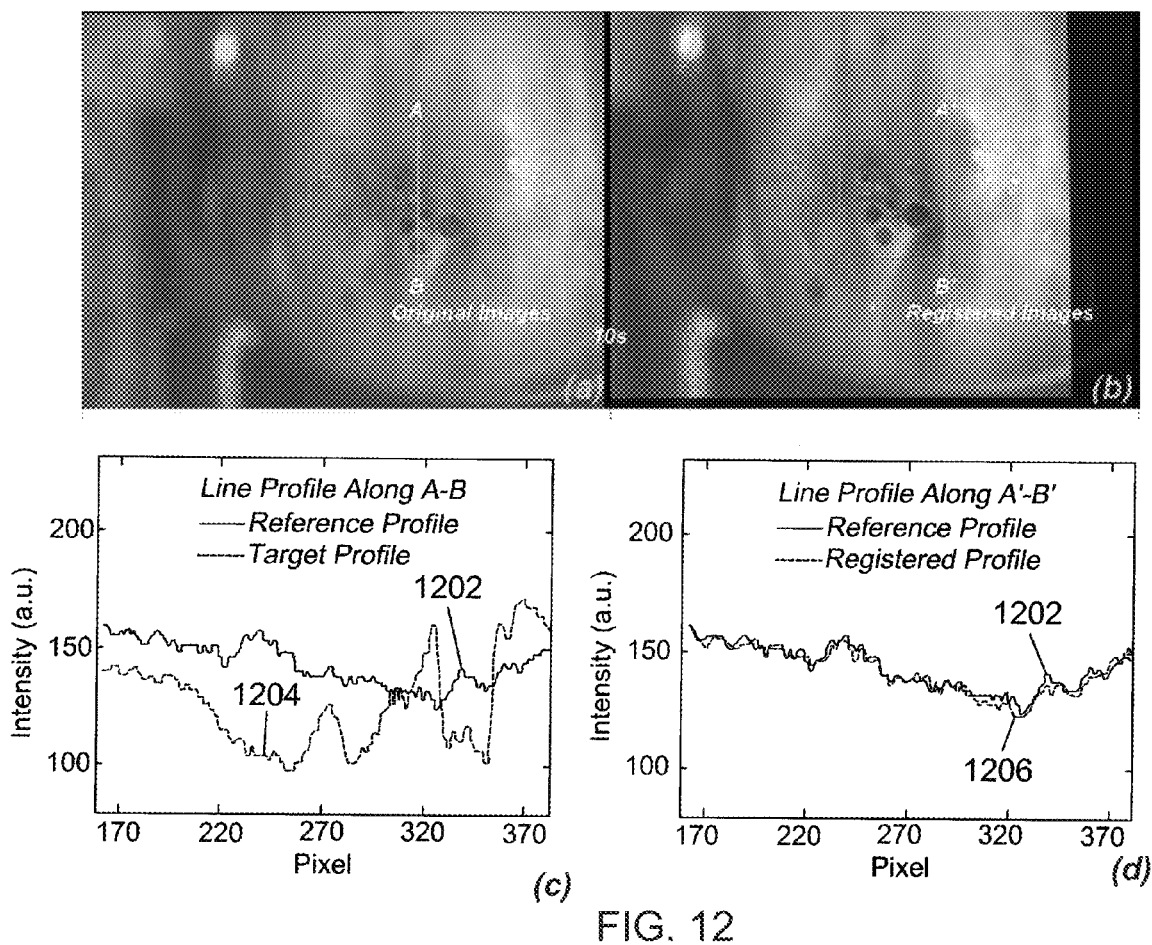
FIGS. 12 (a) through 12 (d) show one representative result of the motion tracking and image registration measured from a human subject having large motions: (a) shows the unregistered target image vs. the reference image; (b) shows the registered target image vs. the reference image; (c) shows the intensity line profiles along line A-B in (a); and (d) shows the intensity line profiles along line A'-B' in (b)
Figure 13:
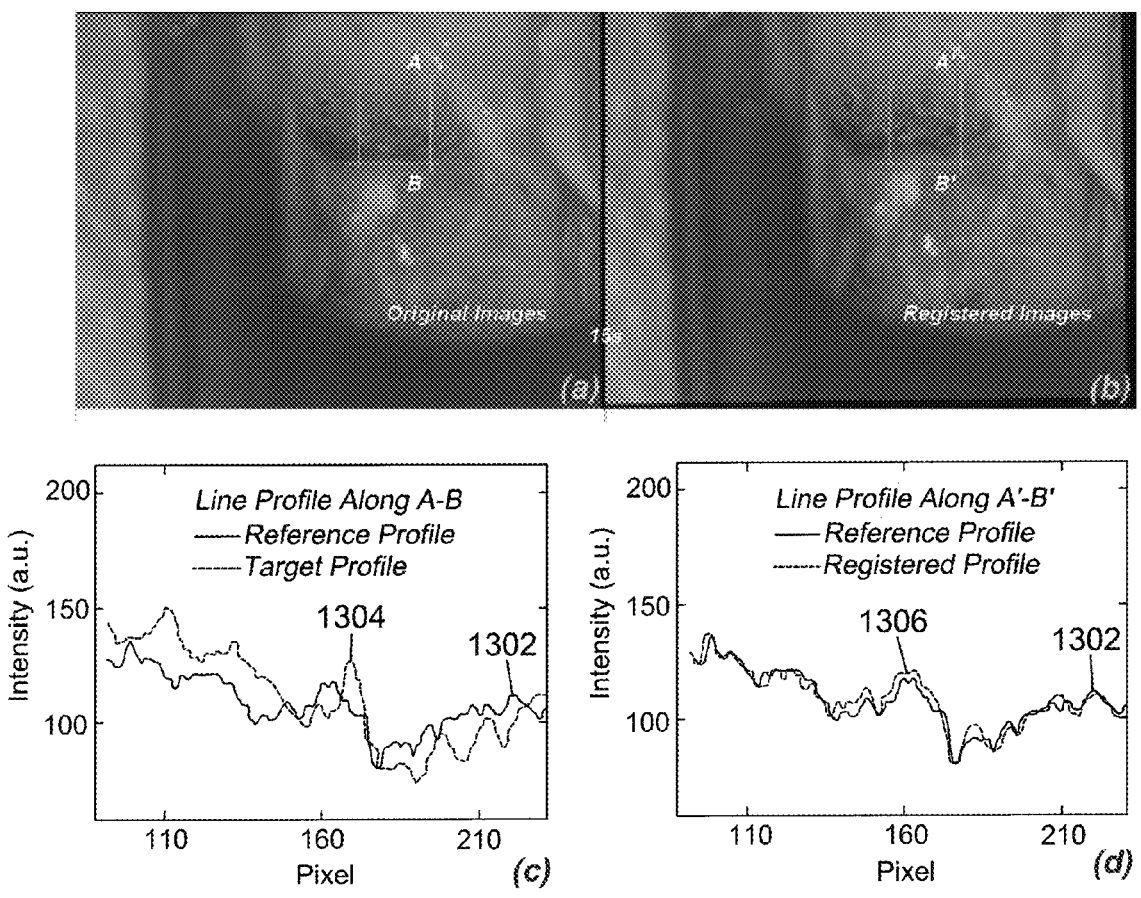
FIGS. 13 (a) through 13 (d) show another representative result of the motion tracking and image registration measured from a human subject having small motions: (a) shows the unregistered target images vs. the reference image; (b) shows the registered target images vs. the reference image; (c) shows the intensity line profiles along line A-B in (a); and (d) shows the intensity line profiles along line A'-B' in (b)

The three-dimensional colposcopic imaging system was evaluated in vivo. Representative results of motion tracking and image registration are shown in FIG. 12 and FIG. 13. The image in FIG. 12(a) shows the superposition of the unregistered target images and a reference image. The target images are the time-sequenced images of the cervix taken over a certain period of time. The reference image is the first image. It should be noticed that all the time-sequenced reflectance images were recorded from the blue channel of the color CCD camera 114. In this case, the maximal movement of the human cervix was about 10 mm. Similarly, the image shown in FIG. 12(b) is the superposition of registered target images and the reference image to show the accuracy of image registration.

In this study, the intensity profiles are computed along a few representative lines measured from the target and reference images. The comparison provides a qualitative evaluation on how accurately the target images are registered to the reference image. As shown in FIG. 12(c), the profile 1204 measured from the unregistered target image along line A-B and the line profile 1202 measured from the reference image are not correlated because of the large motion of the cervix. However, the profiles 1206 measured along line A'-B' from the registered target and reference images shown in FIG. 12(d) closely overlap with each other, indicating the target images are accurately registered to the reference image. The mean distance between the corresponding profile peaks is 1.16±0.92 pixels after image registration. It should be emphasized that the effectively registered area in the target images are that sampled by the structured light in the reference image. The image out of the sampling area cannot be accurately registered due to lacking of surface information. The image shown in FIG. 13 presents the results of tracking and registration of relatively small movements of the patient. Similarly, the mean distance between the corresponding profile peaks is 1.36*1.06 pixels after image registration. Again, it was demonstrated that the three-dimensional colposcopic imaging technique can accurately track the patient's motion and register the two-dimensional images recorded during the examination.

Figure 14A:
FIGS. 14 (a) and 14 (b) shows one representative result of the motion tracking and image registration measured from a human subject based a digital imaging processing method without using the 3-D tracking information: (a) shows the unregistered target image vs. the reference image; and (b) shows the registered target image vs. the reference image.
Figure 14B:

As discussed earlier, a digital image processing method can be used to register the two-dimensional images. FIGS. 14(a) and (b) show one representative result of motion tracking and image registration measured from a human subject using a digital imaging processing method without relying on the three-dimensional information. FIG. 14 (a) shows the unregistered target image vs. the reference image; FIG. 14 (b) shows the registered target image vs. the reference image. As shown in the figures, the two-dimensional images are accurately registered using the digital image processing method. According to this embodiment, the digital image processing method without using the 3-D information is effective when the motion of the patient is very small and the acetowhitening change is not obvious.

Figure 15:
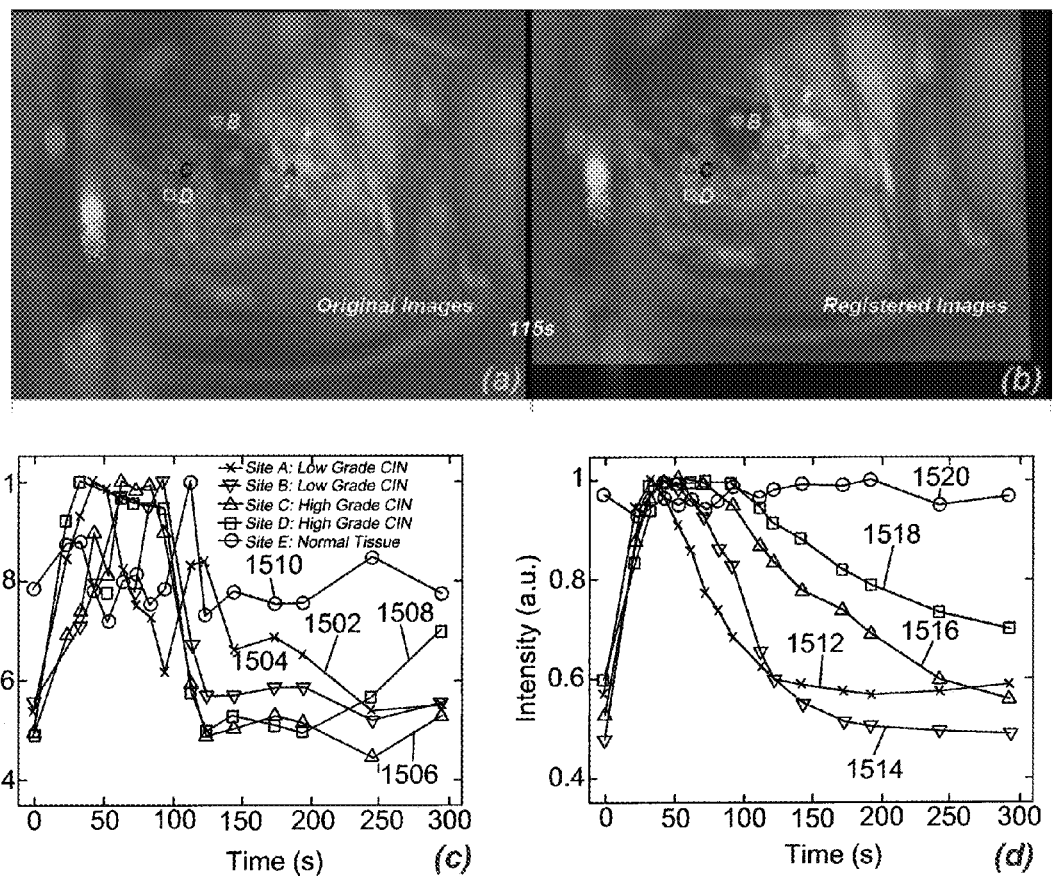
FIGS. 15 (a) through 15 (d) shows the kinetics of the acetowhitening measured from a human subject in vivo: (a) shows the unregistered image vs. the reference image; (b) shows the registered image vs. the reference image; (c) shows the normalized reflection intensity as a function of time measured from 5 sites indicated by A, B, C, D, and E in the unregistered target images in (a); (d) shows the normalized reflection intensity as a function of time measured from 5 sites indicated by A, B, C, D, and E in the registered target images.

The representative results of the measurement of temporal kinetics of acetowhitening are shown in FIG. 15. The images in FIGS. 15(a) and (b) are formed in the same way as those in FIGS. 12 and 13. The target images are taken over 5 minutes after the application of acetic acid to the cervix. The reference image is the image taken at 95 second after the application of acetic acid because the sampling area on cervix was maximal. The changes of acetowhitening are measured as a function of time at 5 different sites of cervix from the unregistered and registered target images, respectively. The sampling area at each measurement site includes 6×6 pixels in image, equivalent to an area of 0.3×0.3 mm on the cervix. It is sufficiently small compared with the CIN lesion of a normal size of a few mm. The results are shown in FIGS. 15(c) and (d). As can be seen, the reflection intensity as a function of time (curves 1502-1510) shown in FIG. 15(c) do no provide information on kinetics of the acetowhitening at all because of patient's movements, while the curves (curves 1512-1520) displayed in FIG. 15(d) demonstrate that reflection signals as a function of time follow a smooth pattern. Curves 1502 and 1512 are the reflection signals from site A. Curves 1504 and 1514 are the reflection signals from site B. Curves 1506 and 1516 are the reflection signals from site C. Curves 1508 and 1518 are the reflection signals from site D. Curves 1510 and 1520 are the reflection signals from site E.

Normally, the grade of the CIN lesion varies through the entire cervix surface. The results shown in FIG. 15(d) demonstrate multiple kinetics of the acetowhitening measured at different tissue sites. The diagnoses of the tissues at 5 different measurement sites labeled in FIG. 15(b) by two colposcopists show that sites A and B are CIN 1 (i.e., low grade lesion), sites C and D are CIN 2-3 (i.e., high grade lesion) and site E is normal.

Figure 16:
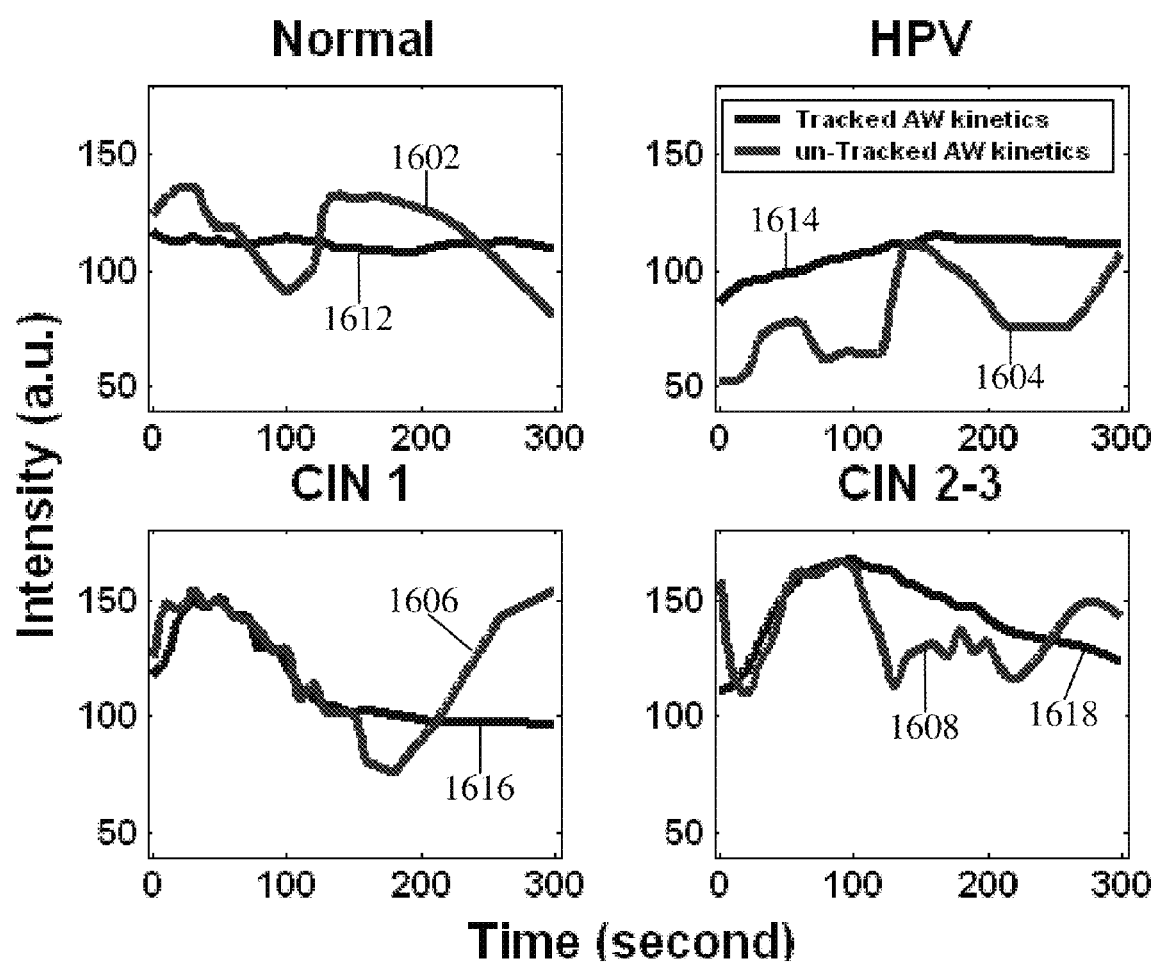
FIG. 16 shows the acetowhitening kinetics with and without tracking.

As a comparison, without image registration, the measurement of the acetowhitening kinetics using the time-sequenced images generates false diagnostic information. As shown in FIG. 16, the reflection intensity as a function of time shown in curves 1602-1608 do not provide information on kinetics of the acetowhitening at all due to patient's movements, whereas curves 1612-1618 demonstrate that the reflection signals as a function of time follows a smooth pattern.

Figure 17:
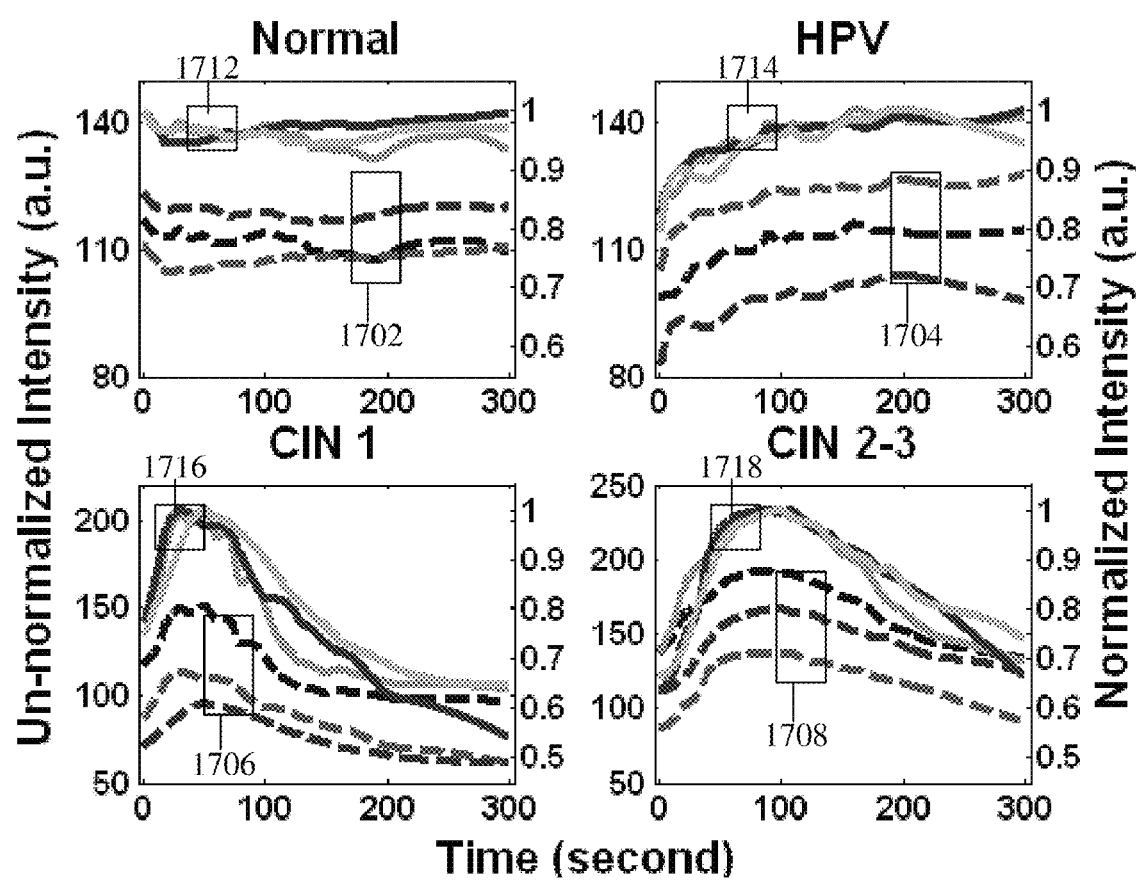
FIG. 17 shows the tracked acetowhitening kinetics with and without normalization to the peak value, where the solid curves indicate the normalized acetowhitening kinetics and the dash curves indicate the un-normalized acetowhitening kinetics.

To prepare the data for data processing, each tracked acetowhitening signal is normalized to its maximum to eliminate the individual-to-individual variation. Typical unprocessed curves 1702-1708 and preprocessed curves 1712-1718 acetowhitening kinetics signals are shown in FIG. 17. As shown in FIG. 17, the intensities of the acetowhitening signals vary across a wide range because of variations in measurement conditions including illumination power, separation of the colposcope from tissue, and incident or emission angles over the images tissue surface from individual to individual and from measuring site to site for each individual. Normalization can reduce the intra-category variation and, thus, enhance the difference of acetowhitening kinetics between normal and abnormal tissue.

To investigate possible correlation between the acetowhitening kinetics and tissue pathology, the kinetics of the acetowhitening are measured from the registered time-sequenced images recorded from 137 sites of 57 patients and are related to the diagnoses made by pathologic reports. For each patient the kinetics of the acetowhitening are measured from 2-3 sites that are diagnosed as four different types of tissues: 12 normal tissue, 66 human papillomavirus (HPV) infected tissue, 15 low grade lesion (CIN 1) and 44 high grade lesion (CIN 2-3), respectively.

Figure 18:
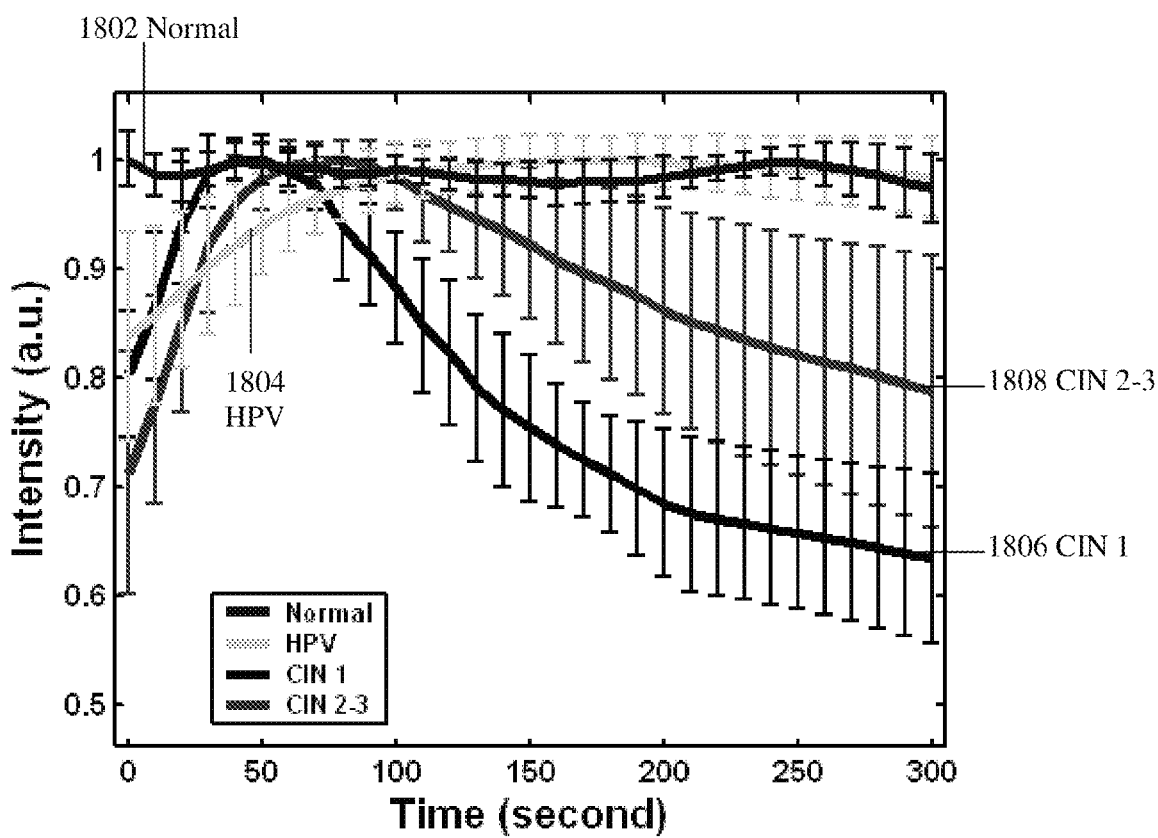
FIG. 18 shows the kinetics of acetowhitening for normal tissue, HPV infection, low and high grade CIN lesions.

Based on the measurements from the 57 patients, the kinetics of the acetowhitening associated with four types of tissues are extracted and the statistical results are displayed in FIG. 18. As seen in FIG. 18, the kinetics of acetowhienting measured from different types of tissues are distinct. The reflection intensity from normal tissue (curve 1802) remains almost unchanged over the measurement period time of 5 minutes. The signal from the HPV infected tissue (curve 1804) increases to the maximum in 100 seconds and stays at the level during the measurement period. The signal from the low grade lesion (curve 1806) increases quickly after the application of the acetic acid and reaches to its maximum in about 50 seconds. The signal then decreases quickly after reaching to the peak. Similar to the signal from the low grade lesion, the signal from the high grade lesion (curve 1808) increases quickly and reaches to its peak in about one minute after the application of the acetic acid. However, the decay of the acetowhitening in high grade lesion is much slower than low grade lesion. Statistically, significant differences between the curves of four different kinetics are found. To quantify the similarity between four different kinetics of the acetowhitening, the correlation coefficient $|r|$ between each two of them are calculated. The $|r|$ between normal and the HPV infected tissue is 0.27. The $|r|$ between normal tissue and the low and high grade lesions are 0.28 and 0.05, respectively. The $|r|$ between the HPV infected tissue and the low and high grade lesions are 0.59 and 0.14, respectively. The $|r|$ between the low grade lesions and the high grade lesions is 0.71. Normally, the absolute value of a correlation coefficient over 0.8 implies a strong linear relationship. The lower r-values suggest that the kinetics of the acetowhitening provide clear differentiation between four types of tissues.

Data Classification for CIN Lesion Grading

To develop a fully objective computer-aided diagnostic system to distinguish the CIN lesions from non-CIN cervix tissue for the screening purpose or distinguish the high grade CIN lesions from other types of cervix tissue for the diagnosis purpose, it is desired to develop an effective classification method to grade the different tissue or lesions. According to one embodiment, a method utilizing the principal component analysis (PCA) is provided for analyzing the statistical characteristics of the acetowhitening process to classify and grade the CIN lesions and non-CIN tissues. Alternatively, another method utilizing the support vector machine (SVM) is provided.

Specifically, the PCA is an effective method for analyzing the statistical characteristics of multi-dimensional data. Since the time resolved acetowhitening kinetics are multi-dimensional signals represented in time domain, multivariate statistical analysis can be utilized for the classification purpose. In general, the PCA technique reduces the dimension of the kinetics signals into a set of informative orthogonal principal components (PCs) that comprise a small number of variables for fully describing variations in the acetowhitening signals within the limitations of noise. The first principle component accounts for as much of the variability in the data set as possible, and each succeeding component accounts for as much of the remaining variability as possible. The diagnostic method uses the reduced set of principle components to extract the principal differences between normal and abnormal tissues for the diagnostic purposes. In the application of the PCA method for processing acetowhitening kinetics, the original time-resolved acetowhitening signals are transformed into new sets of linear combinations of the principle components, principle component scores, in the space of the original time-resolved signal variables. Each principle component score is thus a projection score of the acetowhitening signals to the principle component. The principle components are arranged in the order of their contribution to the variance of the entire time data set.

Figure 19A:
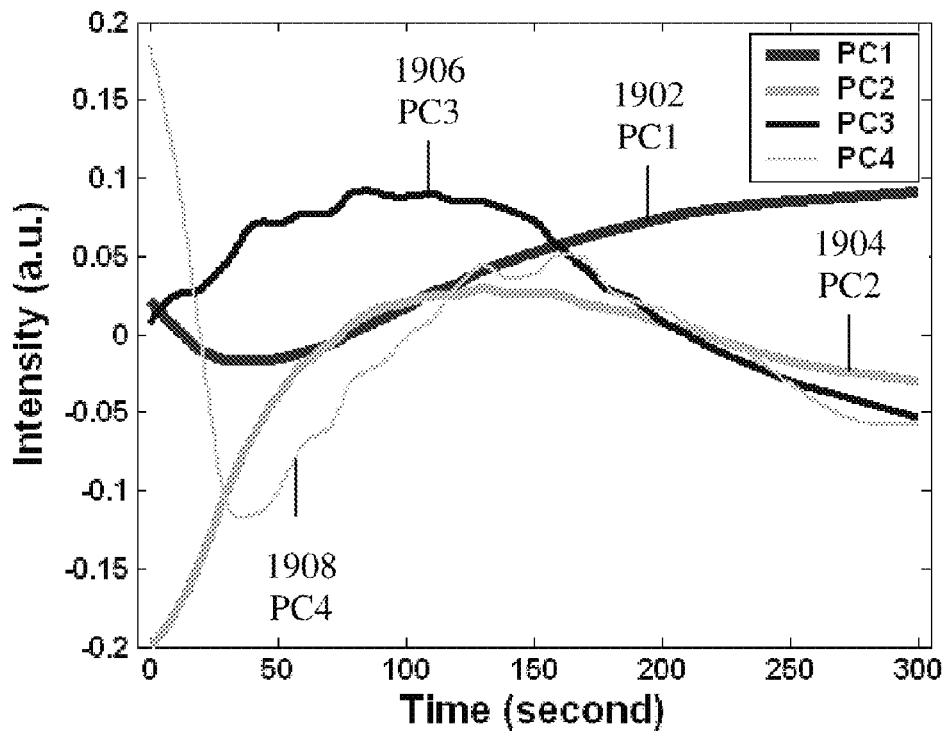
FIGS. 19 (a) and 19 (b) shows (a) the plot of the loading value of the first four principal components and (b) the SCREE plot illustrating the variation according to the first five principal components.
Figure 19B:
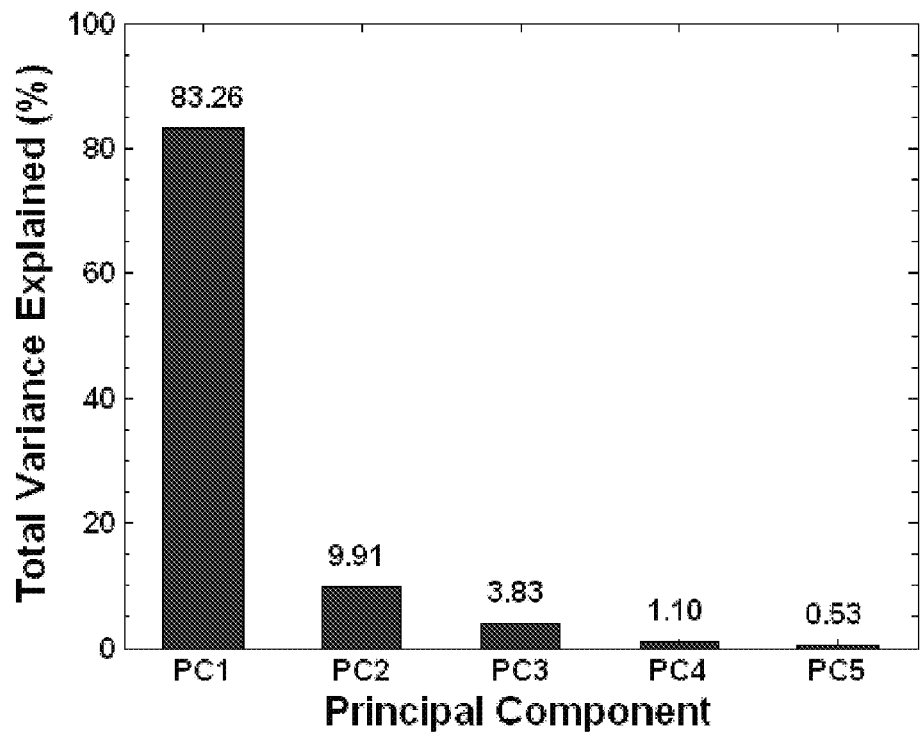

To apply the PCA method for the classification, the principle components were first calculated from the 137 acetowhitening kinetic curves to identify those of diagnostic relevance. The first four principal components (curves 1902-1908) obtained from all the acetowhitening data are shown in FIG. 19($a$). The principle component loadings are significant because they are the "models" trained by the training set and are commonly used by new observations to calculate the principle component scores for diagnosis. From the PC1 loading curve 1902 shown in FIG. 19($a$), it can be observed that there is a slow increase loading value after the 50-second region. This implies that the first principle component mainly captures the increasing acetowhitening kinetics of the HPV infected tissue. From the principle components loading, a fast increasing loading and a slow decay loading value at the region of 0-100 seconds and that of 100-300 seconds, respectively, implies that the PC2 curve 1904 captures the acetowhitening kinetics of high grade CIN lesions. Higher order principle components do not have an obvious loading value because they are not significant for diagnosis.

For the principle component score based method, the proportion of variations explained by the principle components determines the number of principle components suitable for analysis. The contribution of each principle component to the total variance of acetowhitening kinetics signals is proportional to its eigenvalue. The proportions of variation explained by the first five principle components are shown in the SCREE plot in FIG. 19($b$). A SCREE plot is a plot of eigenvalues against the component number. The SCREE plot illustrates the fact that the first two principle components are enough to account for 93% of the data variation. The higher order principle components account for less than 4%, and therefore are not significant for diagnosis. Since most of principle components account mainly for noise and do not provide diagnostic information, it is necessary to identify a small group of informative principle components for classification of the acetowhitening signals. The complexity of a diagnostic algorithm will be reduced by including a minimal number of principle components. This result shows that using two principle components are enough to extract significant data variation for diagnosis. Hence, it is reasonable to use only the first two principal components for tissue classification.

Figure 20:
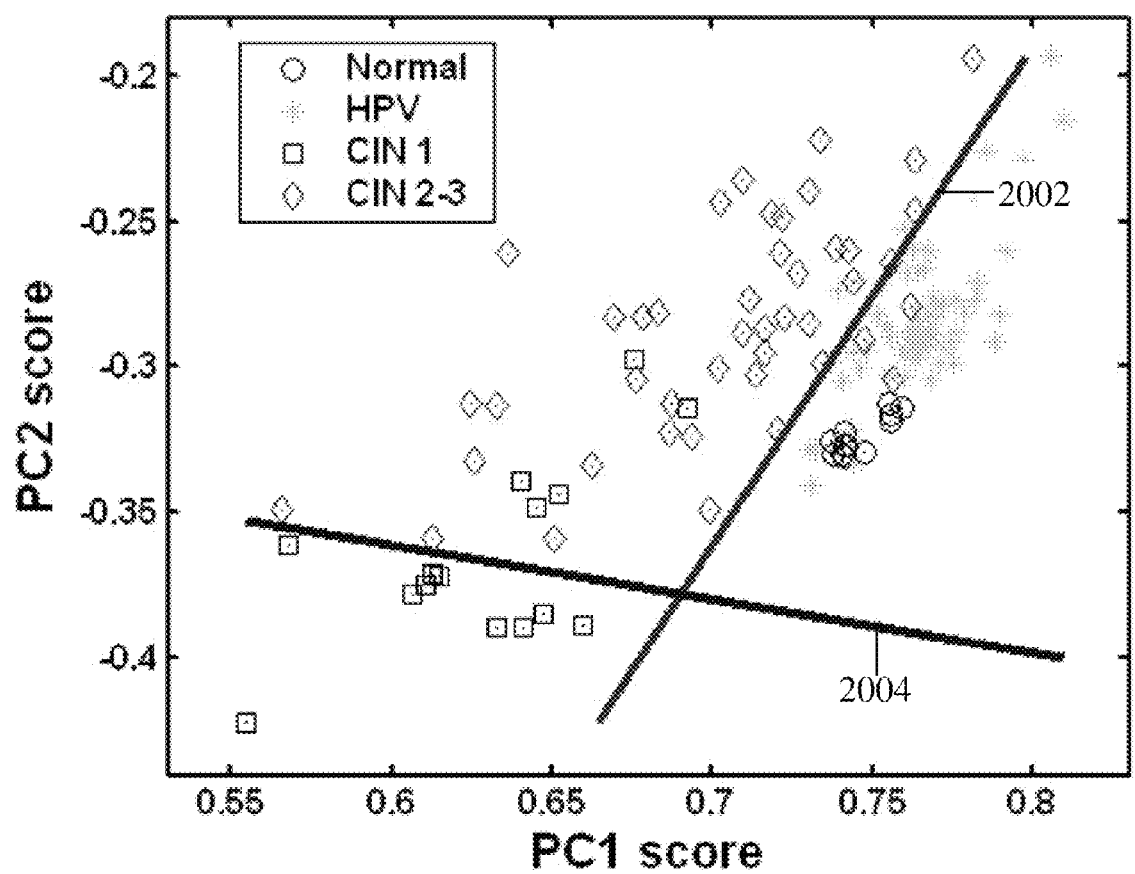
FIG. 20 shows a scatter plot of the PC1 and PC2 scores, where the line 2002 indicates the algorithm classifying the acetowhitening process of the CIN lesions from non-CIN tissue with a sensitivity of 95% and a specificity of 96% and the line 2004 plus the line 2002 indicate the algorithm classifying the acetowhitening process of the CIN 2-3 lesions from other tissue types with a sensitivity of 91% and specificity 89%.

The scatter plot of the PC1 and PC2 scores is shown in FIG. 20. As there is a significant difference between the principle component scores of the CIN lesions and the non-CIN tissue, the classification can be based on the score value. Using a combination of PCA and linear separation, the acetowhitening processes is used to determine whether or not a cervical lesion diagnosis could be made on this basis.

A linear line separation algorithm with the first two principle components is used to classify the in vivo acetowhitening signals based on the correlation between the principle component sores of the acetowhitening signals to the informative principle components and the pathologic state of the tissue sites where the acetowhitening signal is measured. In the two-dimensional space of the PC1 and PC2 scores in FIG. 20, a diagnostic line was developed to separate the scores of the acetowhitening signals from different clusters, e.g., separating the acetowhitening process of the CIN lesions from those of normal and HPV infected tissue, and to create a diagnostic algorithm. Specifically, the diagnostic line is defined as $Y=aX+b$, where X and Y are the PC1 and PC2 scores. The accuracy for separation is controlled by choosing the parameters of a and b. An exhaustive search is performed to determine the values of a and b that maximize the sensitivity corresponding to the highest accuracy, because it is importance to detect more CIN lesions for the prevention of cancer development. As an example, a diagnostic line 2002 classifying the CIN lesions from the non-CIN tissues at a sensitivity of 95% and a specificity of 93% is depicted in FIG. 20. The diagnostic line 2002 divides the data points in FIG. 20 into two sub-areas: the CIN lesions area on the left of the line, and the non-CIN tissues on the right of the line. The classification accuracy is determined by how correctly the diagnostic line 2002 separates the processed acetowhitening signals in FIG. 20 into the corresponding type of tissue.

Evaluation of Data Classification

A trial is conducted to evaluate the method combining PCA and linear separation, which is used to classify the CIN lesions from the non-CIN tissues for the screening purpose. In the validation procedure, one acetowhitening signal is held back and the principle components from the remaining 136 acetowhitening signals are determined. After the diagnostic lines were created, they are used to classify the acetowhitening signal that is held back. This procedure is repeated until all the acetowhitening processes are classified. The final results are presented in Table 2.

TABLE 2

Classification of acetowhitening kinetics with different algorithms for SCREENING purpose: Discrimination of CIN lesions from Normal and HPV infected tissue.

| Algorithms | Sensitivity SE (%) | Specificity SP (%) | Accuracy (%) |
|---|---|---|---|
| PCA + One-Line Separation | 94.9 | 94.9 | 94.9 |
| Linear SVM | 94.9 | 96.2 | 95.6 |
| Non-linear SVM (RBF) | 94.9 | 96.2 | 95.6 |

Using these two principle components and a leave-one-out cross-validation method, 74 of 78 non-CIN tissue and 56 of 59 CIN lesions are predicted correctly. Thus, the CIN lesions can be distinguished with a sensitivity of 95% and a specificity of 95%. In addition, all of the samples diagnosed as normal tissue and the CIN 1 lesions are predicted correctly. 4 of 66 HPV infected tissues are misdiagnosed, so are 3 of 59 CIN 2-3 lesions. Compared with the traditional screening method with less than 50% sensitivity, the PCA algorithm can significantly improve the sensitivity of the diagnosis.

PCA is a commonly used multi-variants method to reduce the dimension of the data and also can be used for the visualization of how the characteristics are different among the examined data. The visualization can make the classification very clear and easier to understand. A linear classification method is commonly applied in most situations. But in more complicated cases, linear separation may not be enough. More effective and accurate classification method is desirable. According to an alternative embodiment, a Support Vector Machine is used to achieve the classification. The SVM is a new method for classifying multivariate data and is more efficient than the PCA algorithm when the separating boundary is nonlinear. Generally, the SVM maps the sample data with specific kernel functions to a higher dimensional feature space to linearize the boundary and generate an optimal separating hyperplane.

In the SVM learning and testing procedure, each time-resolved acetowhitening process is treated as a vector with 301 dimensions and labeled according to the result of the histological examination. Specifically, normal and HPV infected tissue are labeled as −1 and CIN 1 and CIN 2-3 lesions are labeled as +1 for the screening purpose. Diagnostic parameters based on linear and non-linear SVMs are determinated. The performance of the SVM method is evaluated with the leave-one-out and leave-half-out cross-validation.

The optimized algorithms developed from the training set are used to classify the acetowhitening process. This procedure was repeated until all 137 samples are classified. The results of the classifications of all the in vivo acetowhitening signals using linear and non-linear SVM algorithms and leave-one-out cross-validation are summarized in Table 2. It can be found from the table that, the accuracy of the linear and non-linear SVM algorithms for classification of the non-CIN tissue from the CIN lesions is the same. The sensitivity and specificity are 95% and 96%, respectively. The specificity is only slightly higher than that of the PCA method. From the scatter plot of the principle component scores shown in FIG. 20, it can be found that, after some data processing, such as calculating the principle component scores, the separation boundary of the CIN lesions and the non-CIN tissue can be a linear boundary. Through this visualization in FIG. 20, it is easy to imagine that the SVM method can also generate a classification boundary in linear. So the classification accuracy proved by the PCA algorithm and linear/non-linear SVM algorithms is almost the same as that shown in Table 2.

To further simulate the real situation in clinical, the non-linear SVM is evaluated by using the leave-half-out cross-validation. 68 samples are randomly chosen as the training to provide the training parameters and the remaining 69 samples are diagnosed to evaluate the performance of the SVM method. After $4 \times 10^5$ runs, the worse sensitivity and specificity are 70% and 72%, respectively, and the mean sensitivity and specificity are 97% and 96%, respectively. The accuracy is higher than the accuracy of the traditional colposcopy previously reported. This demonstrates that the acetowhitening process can provide accurate screening information for the classification of CIN lesions from normal and HPV tissue.

In another trial, the PCA and SVM methods are used to classify the high grade CIN lesions (CIN 2-3) to low grade lesions (CIN 1) and the non-CIN tissue for the diagnosis purpose.

As seen in FIG. 20, it is impossible to discriminate the high grade CIN lesions from other type of tissue with a linear boundary. However, this classification can be accomplished and simplified by repeating this linear separation two times. Firstly, all CIN lesions are differentiated from other tissue types as in the first trial using the method combining PCA and linear separation. Secondly, another diagnostic line 2004 is determined as shown in FIG. 20 to separate the high-grade CIN lesions from the low-grade CIN lesions. With this two-line PCA algorithm and leave-one-out cross-validation, we can obtain sensitivity of 91% and specificity 89% for the separation of CIN 2-3 lesions from other tissue types. Further, the linear and non-linear SVM methods are used for diagnostic classification. The linear SVM method cannot provide classification as accurate as those provide by the two-line PCA method. The sensitivity and specificity of leave-one-out cross-validation are 89% and 83%, respectively. However, the non-linear SVM method can generate a comparable result to that of the two-line PCA method, which demonstrates that a non-linear boundary is generated to differentiate the CIN 2-3 lesions from other tissue types at one time.

The results using the PCA and SVM methods based on the leave-one-out cross-validation are summarized in Table 3.

TABLE 3

Classification of acetowhitening kinetics with different algorithms for DIAGNOSIS purpose: Discrimination of CIN 2-3 lesions from Normal, HPV infected tissue and CIN 1 lesions.

| Algorithms | Sensitivity SE (%) | Specificity SP (%) | Accuracy (%) |
|---|---|---|---|
| PCA + Two-Line Separation | 90.9 | 89.3 | 89.8 |
| Linear SVM | 88.6 | 82.8 | 84.7 |
| Non-linear SVM (RBF) | 90.9 | 90.3 | 90.5 |

The accuracy of the methods for diagnostic purpose is lower than those for screening CIN lesions. This is caused by part of the CIN 1 lesions being mixed together with the CIN 2-3 lesions. In fact, it is difficult to exactly classify the CIN lesions in histological examinations because the grade of CIN lesions is based on a series of subjective criteria. In addition, there are only 15 CIN 1 lesions out of 137 cases in this study. When the sample size of the CIN 1 lesions is small, one or two misclassifications of the CIN 1 lesions will reduce the specificity significantly. Collecting more samples of CIN 1 lesions will make the classification method more robust. Overall, the classification results of the PCA and SVM method demonstrate that the colposcopy imaging technique described herein can provide objective and quantitative colposcopic diagnosis. The screening accuracy to discriminate CIN lesions from normal and HPV-infected tissues and the diagnosis accuracy to discriminate high-grade CIN lesions from low-grade CIN lesions, the HPV and the normal tissue are higher than the reported sensitivity and specificity of conventional methods such as Pap smear and colposcopy.

The results also demonstrate that the imaging technique described herein can accurately track the patient's motion and register the 2-D images of the cervix recorded during colposcopy in vivo. The acetowhitening process in the imaged tissue can be quantitatively mapped based on the registered time-sequences images of the cervix. The distinct differences in the acetowhitening processes between the normal tissue, the HPV infection and the low/high grade CIN lesions provide solid basis for quantitative diagnosing and grading of cervical precancerous lesions. The quantitative imaging method can be used in conjunction with the traditional colposcopy to improve the diagnostic accuracy of colposcopy. In addition, the system shown in FIG. 8 can be used in the standard colposcopy and the mapping of the acetowhitening process over the imaged tissue surface simultaneously. Therefore, the diagnostic instrument and methods could be inserted into the physician's workflow with minimal interference with the routine colposcopy procedure.

Applications in Endoscopy

The imaging system and method described herein can be used in other applications such as examining and imaging oral cavity, skin, and internal organs including the esophagus where the acetic acid is used as a contrast enhance reagent. This imaging technique can also be used in other circumstances where the registration of time-sequenced images of a subject is desired. According to various embodiments, the structured light can be integrated in an endoscope for three-dimensional imaging of the internal organs. So the optical imaging system and method can be used for the diagnosing the precancerous of internal organs.

Figure 21:
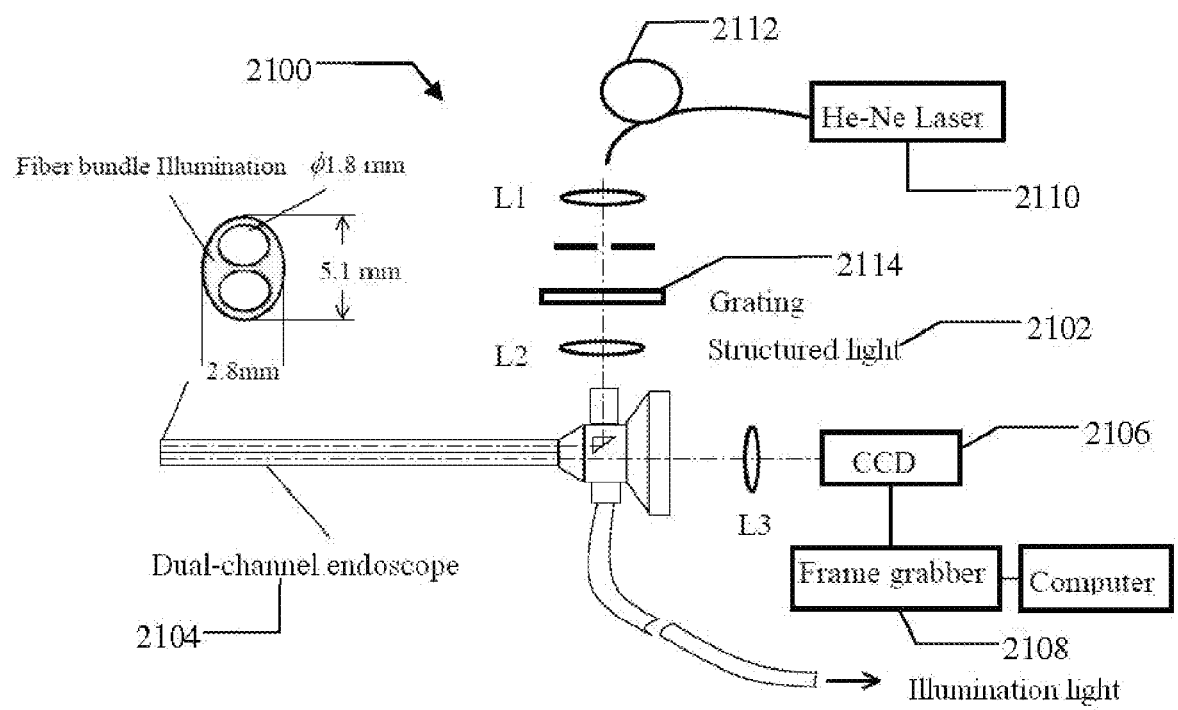
FIG. 21 shows the schematic view of the dual-channel endoscopic imaging system.

One embodiment of the endoscope 2100 is shown in FIGS. 21. A custom-made rigid endoscope 2100 with dual-imaging channels 2104 is utilized to project structured light 2102 with a known pattern on the scene and to image the pattern to recover three-dimensional information about the imaged surface. Each imaging channel is 1.8 mm in diameter. The full view angle of each channel is approximately 50 degree. The separation of the optical axes between the two channels was approximately 2 mm. The space between the imaging channels and the protective tubing is filled with optical fiber to conduct light illumination during endoscopy. The image of the object is taken through the imaging channel and recorded with a CCD camera 2106. An image-processing board (i.e., frame grabber 2108) is used to capture the images. The light from a lower-power He—Ne laser 2110 is coupled into an optical fiber 2112 and is collimated by lens L1 and conducted to illuminate the holographic binary phase grating 2114. The structured light 2102 with 64×64 dot matrix pattern is generated with the holographic binary phase grating 2114 and the collimated light. Here, the holographic binary phase grating 2114 acted as a beam splitter to diffract the collimated illumination into multiple beams with a fixed separation angle between adjacent beams. With appropriate focusing, the diffracted beams can be projected to the imaged object and form a fine dot matrix that provides ideal feature points for the three-dimensional measurement of a surface profile. The number of diffracted beams is determined by the design and structure of the grating. By increasing the number of split beams, more feature points are available to sample the surface of the imaged object and higher accuracy of the 3-D measurement can be achieved.

Evaluation of the performance of the endoscopic imaging system for the three-dimensional measurements is conducted after the calibration of both channels. First, a target with a plane feature is used to evaluate the accuracy of the depth measurement. The percentage of measurement errors of the separation between the endoscope and the plane of the target is less than 2% when the separation ranged from 15 to 45 mm. In the second experiment, a step target was used to evaluate the reconstruction of the flat surface at different angles. As a result, the structure of the step target is recovered accurately at different view angles. The last target to be used to evaluate the accuracy of the three-dimensional measurements is a curved object made with a pair of cylinders attached to each other. The percentage error of the feature points to the fitted cylindrical surfaces is 2.7%, which demonstrates that the three-dimensional endoscopic system can recover a curved surface accurately.

Figure 22A:
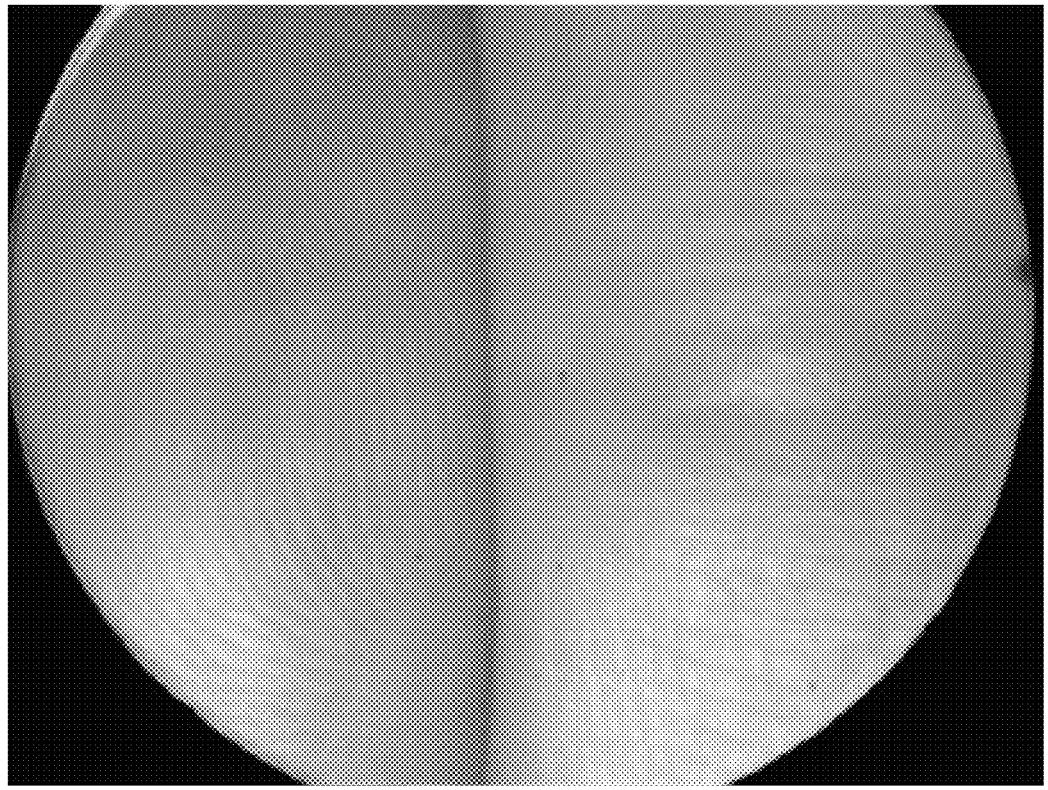
FIGS. 22 (a) and 22 (b) shows (a) the human finger tissue under investigation and (b) the dot patterns projected onto the surface of the human finger tissue.
Figure 22B:
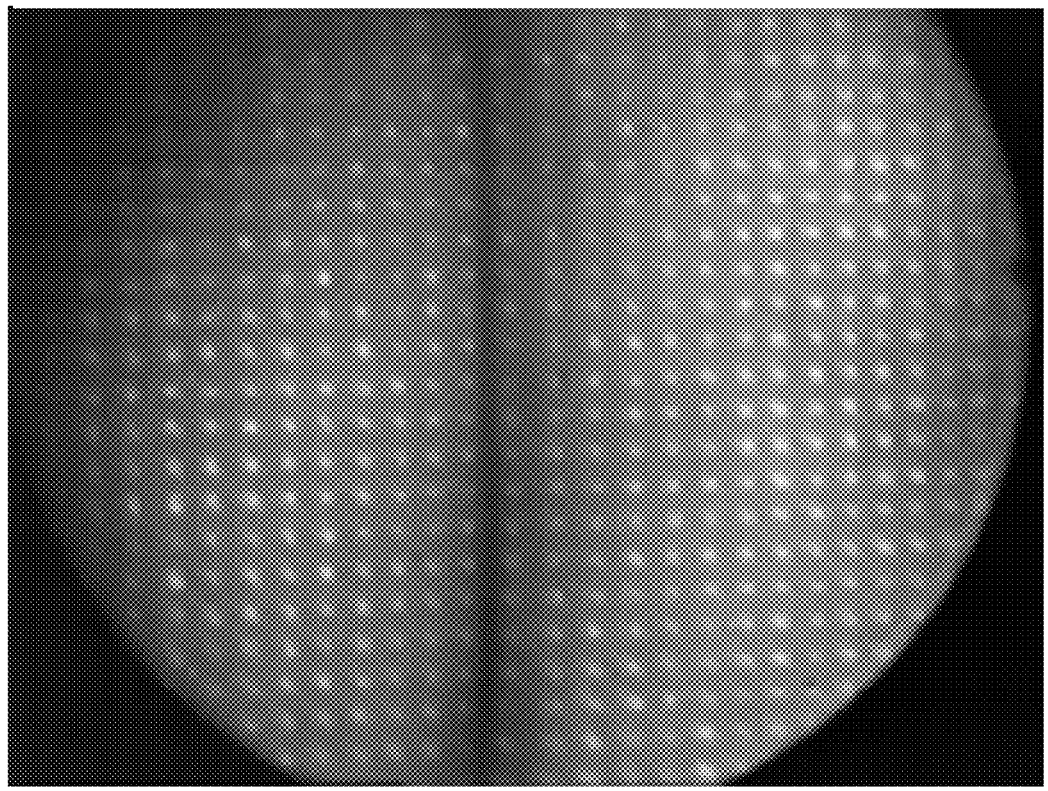
Figure 23:
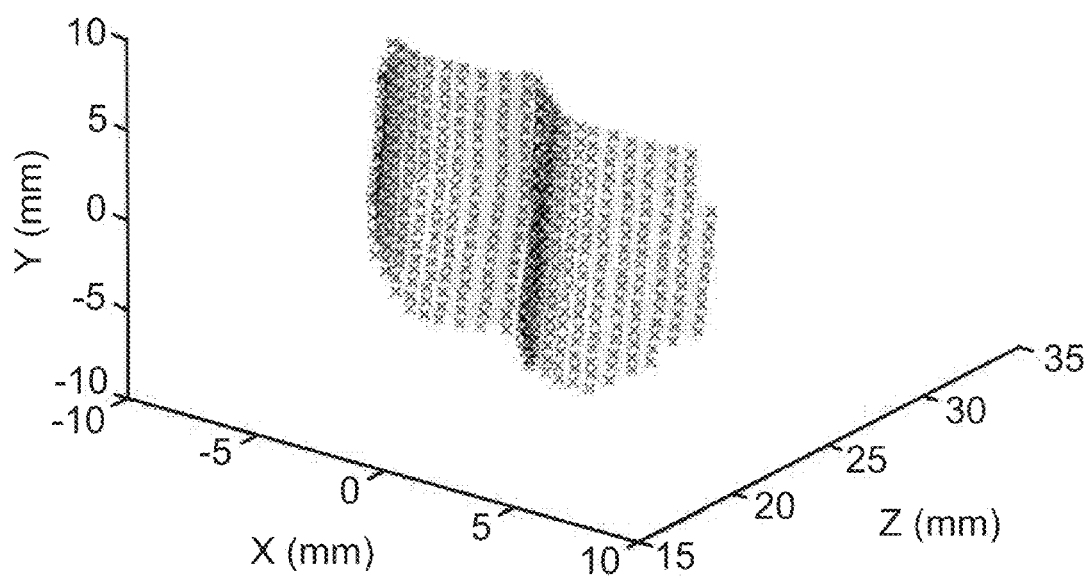
FIGS. 23 (a) and 23 (b) shows the reconstructed 3-D surface of fingers at different view angles.
Figure 23:
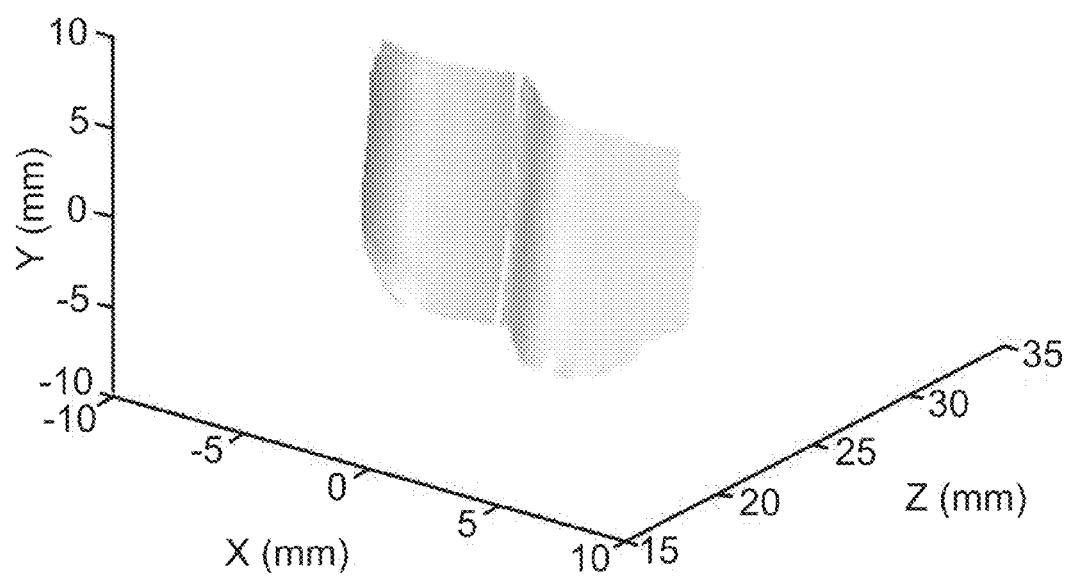
Figure 24A:
FIGS. 24 (a) and 24 (b) shows (a) an image of an oral cavity site for three-dimensional measurements and (b) the image of the tissue site projected with feature points.
Figure 24B:
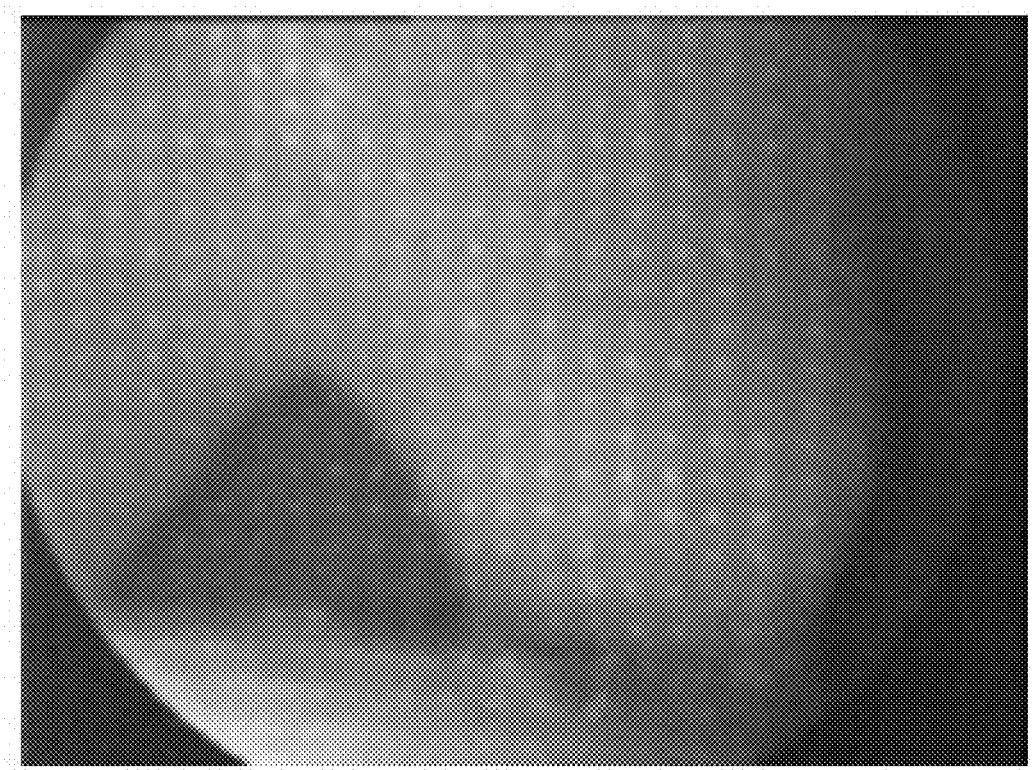
Figure 25:
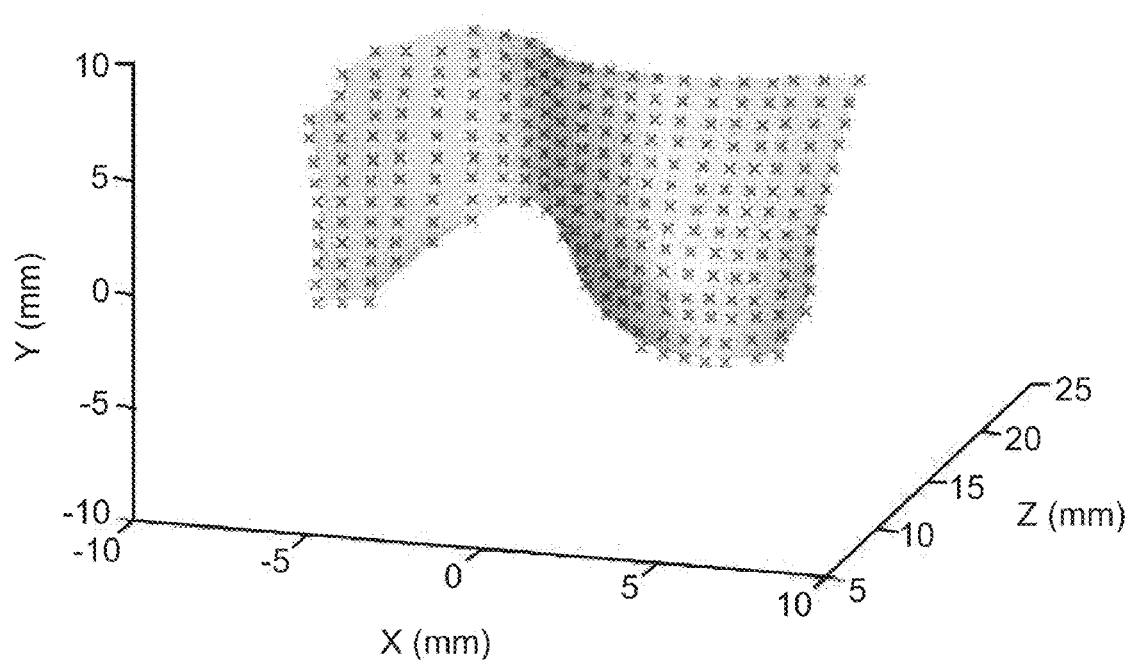
FIG. 25 shows the reconstructed three-dimensional surface of part of the oral cavity at different view angles.
Figure 25:
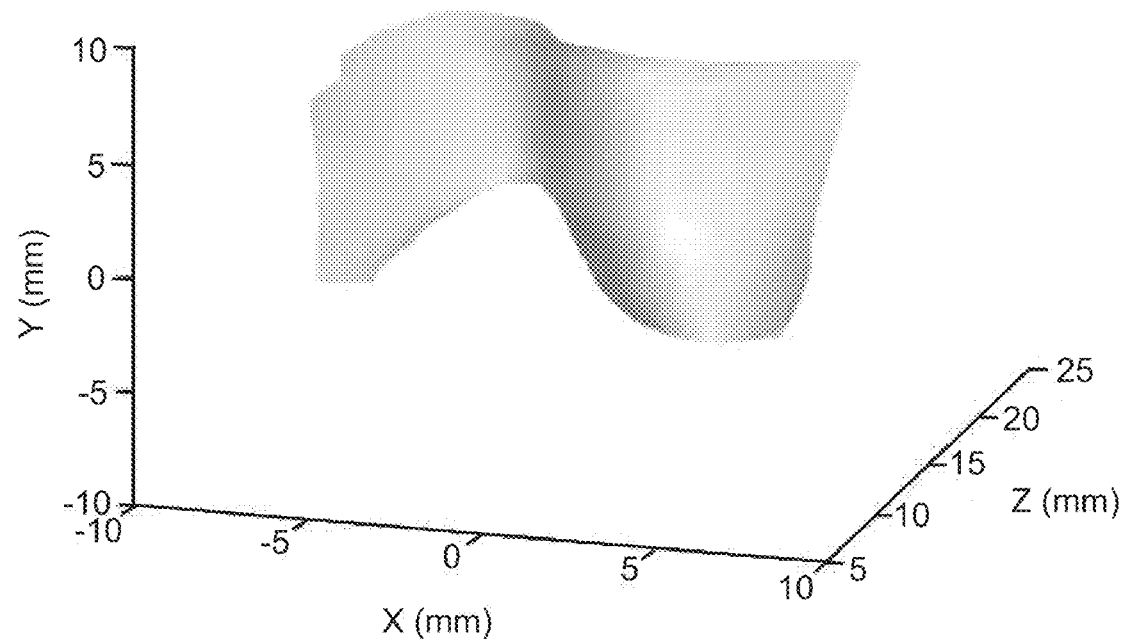

To evaluate the potential of clinical application of the miniaturized three-dimensional endoscopic imaging system, the measurements are conducted on curved tissue surfaces. Here, the surface of the tips of the index and the middle fingers as shown in FIG. 22 was first recovered by use of the three-dimensional endoscopic imaging system. Then, the surface of part of the oral cavity as shown in FIG. 24 was examined with the endoscope. The reconstructed surfaces of the fingers and part of the oral cavity are shown in FIGS. 23 and 25. The recovered sizes of the fingers are shown to be consistent with the approximate measurements taken with a vernier caliper. The projection of reconstructed 3-D surfaces to the X-Z plane in FIG. 25 demonstrates that the depth information of the tissue surfaces has been recovered.

Described herein is an optical imaging method and system for conducting objective colposcopic or endoscopic diagnosis for early detection of cancers. Various embodiments described herein provide quantitative diagnostic information, that is critical to cancer prevention and management in the regions where screening equipment and professional physicians are in short supply.

Computer Programs for the Imaging System

According to the invention, a computer readable medium including computer program codes is provided for carrying out optical imaging in a medical diagnosis such as colposcopy and endoscopy. The computer program codes include the various instructions for data acquisition, image registration, acetowhitening extraction, and data point classification.

Figure 26:
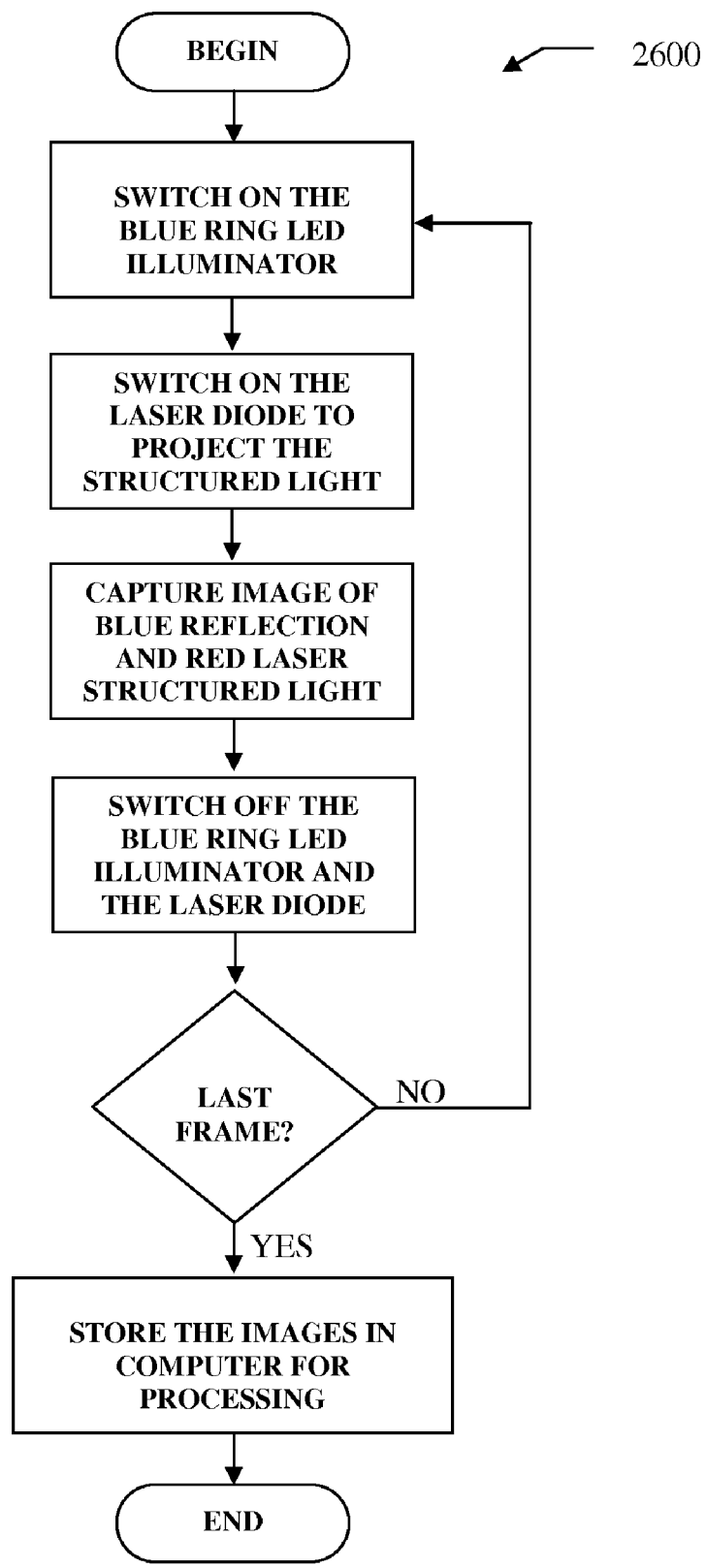
FIG. 26 shows a flow diagram of a method implemented in a computer program for image acquisition.

FIG. 26 depicts a data acquisition program 2600 according to the invention. As shown in FIG. 26, upon initialization, the blue LED light and the LD laser light are turned on and the camera captures the RGB images. One image is captured for every second and a total of 301 images are captured. The images of blue illumination and red laser structured light are captured at the same time and stored in memory for later processing.

Figure 27:
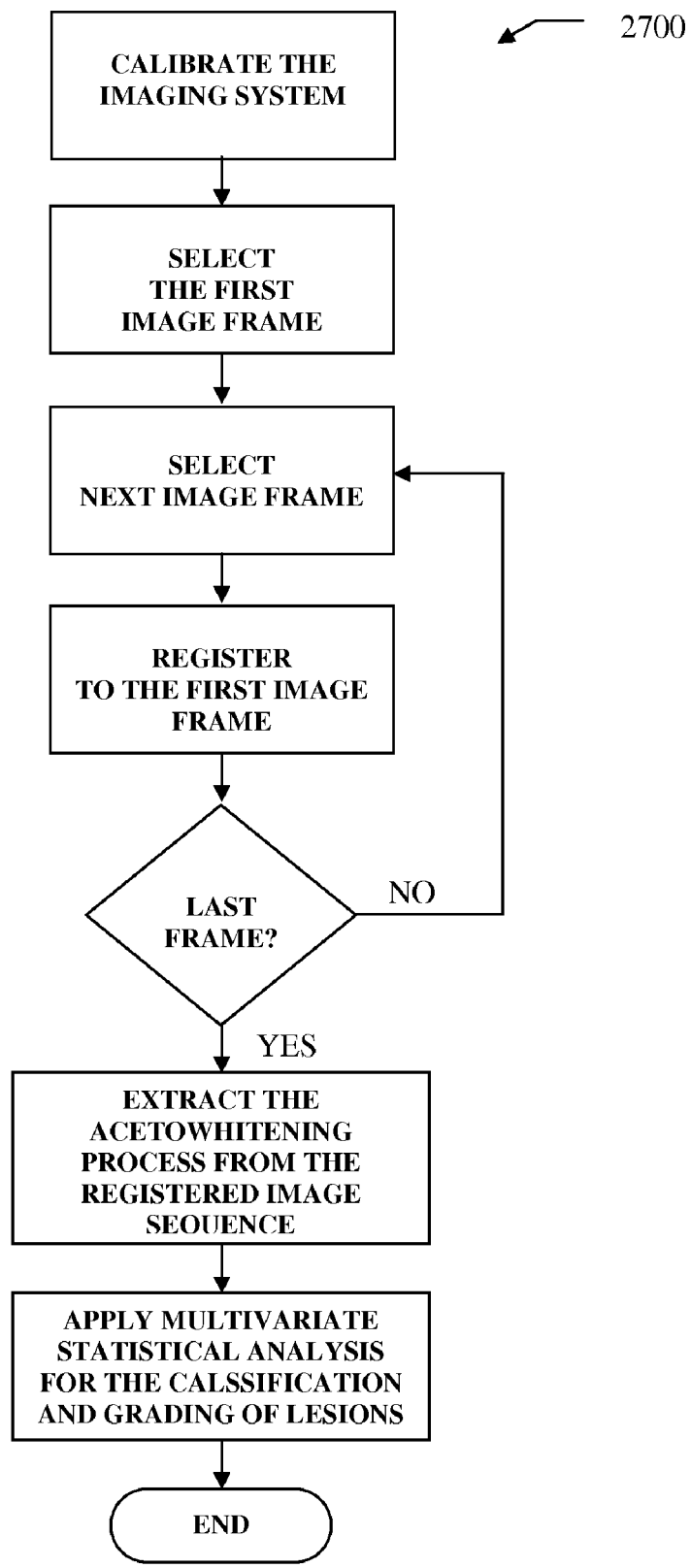
FIG. 27 shows a flow diagram of a method implemented in another computer program for image registration.

FIG. 27 depicts an image registration program 2700 according to the invention. Specifically, the imaging channel and the projection channel in the imaging system are calibrated. The images of blue illumination and red laser structured light are loaded. The 3D surface of the object in each image frame is reconstructed according to the method described earlier. Each of the 3D surfaces extracted from the subsequent images is registered to the 3D surface of the first frame. The 3D surface tracking information is used to register the 2D image series. When all of the images are properly registered, the acetowhitening extraction and data classification are applied to the registered image sequence according to the methods described earlier.

As for acetowhitening extraction, the intensity of the acetowhitening process is extracted as the function of time from the time-sequenced registered images. For data classification, multivariate statistical methods based on PCA and SVM algorithms are applied for the classifying and grading the lesions by using the acetowhitening kinetics information.

The computer programs described above for data acquisition, image registration, acetowhitening extraction, and data point classification are coded using a number of programming languages including C++ and MATLAB on a Microsoft Windows-based system. One skilled in the art will readily recognize that other programming languages and operating systems such as Java, BASIC, FORTRAN, LINUX can also be adopted to implement these computer programs.

Although some exemplary embodiments of the invented are disclosed here, it is not intended to unnecessarily limit the scope of the invention. Thus, simple modifications or variations without departing from the principle or the extent of the claims are still within the scope of the present invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system for providing optical imaging in a medical diagnosis, comprising:
    at least one illuminating light source for generating light illuminating a portion of an object;
    at least one structured light source for providing a projection channel and projecting a structured light-pattern on the portion of the object;
    at least one camera for providing an imaging channel and imaging the portion of the object and the structured light pattern; and
    a computer, configured to:
        calculate by triangulation a three-dimensional topology of the portion of the object based on a correspondence established between the projection channel and the imaging channel;
        perform three-dimensional motion tracking based on the calculated three-dimensional topology; and
        generate a grade corresponding to a lesion of the object based on a multivariate analysis on temporal acetowhitening kinetics measurements performed on an area of the portion of the object corresponding to the lesion.

2. The system of claim 1, further comprising means for performing a diagnosis utilizing the grade.

3. The system of claim 1, further comprising means for removing a specular reflection of the light.

4. The system of claim 1, further comprising means for forming a cross-polarized reflection of the light for the at least one camera to generate at least one cross-polarized image of the portion of the object.

5. The system of claim 1, wherein the at least one camera generates a first and a second images of the portion of the object, the system further comprising means for registering the second image to the first image.

6. The system of claim 1, wherein the temporal acetowhitening kinetics measurements are indicative of at least one of a rapidity of an acetowhitening process, a duration of the acetowhitening process, an amplitude of acetowhitening signals associated with the acetowhitening process, a degree of the acetowhiteness process, a contrast of the acetowhitening process, a sharpness of a demarcation line between precancerous lesions and normal tissues, and a degree of the acetowhitening process when a change of a color of the portion of object reaches a maximum.

7. The system of claim 1, wherein the multivariate analysis includes at least one of a Principle Components Analysis (PCA) and a Support Vector Machine (SVM).

8. The system of claim 1, further including means for detecting the structured light pattern from images generated by the at least one camera.

9. The system of claim 1, wherein the at least one camera generates one or more images of the portion of the object, the system further comprising a frame grabber for capturing and storing the one or more images.

10. The system of claim 1, further comprising means for analyzing a motion of the object in three-dimensional space based on images generated by the at least one camera, wherein the motion of the object has at least one of six degrees of freedom and the six degrees of freedom include three degrees of translations and three degrees of rotations.

11. The system of claim 1, the at least one structured light source comprising:
    a laser light source for generating a laser beam;
    a holographic grating for diffracting the laser beam; and
    one or more reflective surfaces for directing the diffracted laser beam.

12. The system of claim 11, wherein the at least one structured light source is synchronized with the camera.

13. The system of claim 11, wherein the structured light pattern includes one of a group of dots, a group of lines, a dot matrix, a plurality of stripes, and a grid pattern.

14. The system of claim 1, wherein the at least one illuminating light source includes one of a white-light source and a ring light-emitting diode (LED) illuminator.

15. The system of claim 1, further comprising:
    a first linear polarizer for polarizing the light generated by the light source; and
    a second linear polarizer for polarizing at least a portion of the light reflected from the object.

16. The system of claim 15, wherein the polarization of the first linear polarizer is perpendicular to the polarization of the second linear polarizer.

17. The system of claim 1, further comprising an electronic panel and programmable computer ports for automatically switching on and off the at least one illuminating light source and the at least one structured light source.

18. A method for providing optical imaging in medical diagnosis, comprising:
    illuminating a portion of an object;

projecting, via a projection channel, a structured light pattern onto the portion of the object;

generating, via an imaging channel, a sequence of images of the illuminating portion of the object;

calculating by triangulation a three-dimensional topology of the portion of the object based on a correspondence established between the protection channel and the imaging channel;

performing three-dimensional motion tracking based on the calculated three-dimensional topology; and generating a grade corresponding to a lesion of the object based on a multivariate analysis on temporal acetowhitening kinetics measurements performed on an area of the portion of the object corresponding to the lesion.

19. The method of claim 18, wherein the sequence of images includes one or more cross-polarized reflection images of the portion of the object.

20. The method of claim 18, the sequence of images include a first image and a second image, the method further comprising registering the second image to the first image.

21. One or more non-transitory computer readable media including computer codes for instructing one or more digital processor for providing optical imaging in a medical diagnosis, the computer codes including:

instructions for illuminating a portion of an object;

instructions for projecting, via a projection channel, a structured light pattern onto the portion of the object;

instructions for generating, via an imaging channel, a sequence of images of the illuminated portion of the object;

instructions for calculating by triangulation a three-dimensional topology of the portion of the object based on a correspondence established between the projection channel and the imaging channel;

instructions for performing three-dimensional motion tracking based on the calculated three-dimensional topology; and instructions for generating a grade corresponding to a lesion of the object based on a multivariate analysis on temporal acetowhitening kinetics measurements performed on an area of the portion of the object corresponding to the lesion.

22. The one or more computer readable media of claim 21, the computer codes further comprising instructions for performing diagnosis of a precancerous lesion and a cancer on the portion of the object.

23. The one or more computer readable media of claim 21, the computer code further comprising instructions for registering the sequence of images to another image of the portion of the object.

24. The one or more computer readable media of claim 21, wherein the multivariate analysis includes at least one of a Principle Components Analysis (PCA) and a Support Vector Machine (SVM).

25. The one or more computer readable media of claim 21, the computer codes further including instructions for storing the sequence of images in a frame grabber.

\* \* \* \* \*

UNITED STATES PATENT AND TRADEMARK OFFICE
CERTIFICATE OF CORRECTION

PATENT NO. : 8,334,900 B2
APPLICATION NO. : 12/506028
DATED : December 18, 2012
INVENTOR(S) : Qu et al.

It is certified that error appears in the above-identified patent and that said Letters Patent is hereby corrected as shown below:

In the Claims

Column 23, Claim 18, line 6 "established between the protection channel and the"

should read -- established between the projection channel and the --.

Signed and Sealed this
Fifteenth Day of October, 2013

Teresa Stanek Rea
*Deputy Director of the United States Patent and Trademark Office*